(12) United States Patent
Poutiatine

(10) Patent No.: US 10,814,148 B2
(45) Date of Patent: Oct. 27, 2020

(54) METHOD FOR AUTOMATICALLY SELECTING AND PROVIDING SUNSCREEN FOR USERS

(71) Applicant: Sunborn Outdoors LLC, Mill Valley, CA (US)

(72) Inventor: Andrew Poutiatine, Mill Valley, CA (US)

(73) Assignee: Sunborn Outdoors, LLC, Mill Valley, CA (US)

( * ) Notice: Subject to any disclaimer, the term of this patent is extended or adjusted under 35 U.S.C. 154(b) by 0 days.

(21) Appl. No.: 16/171,327

(22) Filed: Oct. 25, 2018

(65) Prior Publication Data

US 2019/0060678 A1   Feb. 28, 2019

Related U.S. Application Data

(63) Continuation-in-part of application No. 15/926,282, filed on Mar. 20, 2018, now Pat. No. 10,149,645, and
(Continued)

(51) Int. Cl.
*A61Q 17/04* (2006.01)
*A61B 5/00* (2006.01)
(Continued)

(52) U.S. Cl.
CPC ............ *A61Q 17/04* (2013.01); *A61B 5/0077* (2013.01); *A61B 5/1032* (2013.01); *A61B 5/441* (2013.01);
(Continued)

(58) Field of Classification Search
CPC ...... A61Q 17/04; A61Q 19/004; G16H 50/30; G16H 40/63; A61B 5/441; A61B 5/7275; A61B 5/1032; A61B 5/442; A61B 5/0077; A61B 5/443; A61B 5/448; G06T 7/0012; G06T 2207/10024; G06T 2207/30088;
(Continued)

(56) References Cited

U.S. PATENT DOCUMENTS 10,561,376 B1 * 2/2020 Kahn ..................... A61B 5/746
2002/0082745 A1   6/2002 Wilmott et al.
(Continued)

*Primary Examiner* — Michael P LaPage
(74) *Attorney, Agent, or Firm* — Run8 Patent Group, LLC; Peter Miller

(57) ABSTRACT

One variation of a method includes: accessing a skin type of a user; predicting a first set of locations occupied by the user during a first future time interval; based on historical ultraviolet irradiance data and the first future time interval, calculating a first predicted unprotected ultraviolet radiation exposure of the user during the first future time interval; calculating a maximum allowable ultraviolet radiation exposure for periods within the first future time interval based on the skin type of the user; calculating a first minimum sun protection factor predicted to reduce the first predicted unprotected ultraviolet radiation exposure to less than the maximum allowable ultraviolet radiation exposure; selecting a first sunscreen formula characterized by a first sun protection factor greater than the first minimum sun protection factor; and shipping the first volume of the first sunscreen formula to the user prior to the first future time interval.

20 Claims, 5 Drawing Sheets

Related U.S. Application Data a continuation-in-part of application No. 15/648,158, filed on Jul. 12, 2017, now Pat. No. 10,139,273, and a continuation-in-part of application No. 15/648,158, filed on Jul. 12, 2017, now Pat. No. 10,139,273.

(60) Provisional application No. 62/577,070, filed on Oct. 25, 2017, provisional application No. 62/473,937, filed on Mar. 20, 2017, provisional application No. 62/473,940, filed on Mar. 20, 2017, provisional application No. 62/434,184, filed on Dec. 14, 2016, provisional application No. 62/404,131, filed on Oct. 4, 2016, provisional application No. 62/380,455, filed on Aug. 28, 2016, provisional application No. 62/361,414, filed on Jul. 12, 2016.

(51) Int. Cl.
*G06T 7/00* (2017.01)
*A61B 5/103* (2006.01)
*G16H 40/63* (2018.01)
*G16H 50/30* (2018.01)
*G06Q 30/02* (2012.01)
*A61Q 19/00* (2006.01)

(52) U.S. Cl.
CPC .............. *A61B 5/442* (2013.01); *A61B 5/443* (2013.01); *A61B 5/7275* (2013.01); *G06T 7/0012* (2013.01); *G16H 40/63* (2018.01); *G16H 50/30* (2018.01); *A61B 5/448* (2013.01); *A61Q 19/004* (2013.01); *G06Q 30/0269* (2013.01); *G06T 2207/10024* (2013.01); *G06T 2207/30088* (2013.01)

(58) Field of Classification Search
CPC ... G06Q 30/0269; G01N 21/33; G01J 1/4204; G01J 2001/4266; G01J 1/429
See application file for complete search history.

(56) References Cited

U.S. PATENT DOCUMENTS

| | | | |
|---|---|---|---|
| 2003/0064350 A1* | 4/2003 | Rubinstenn | G06T 11/00 434/99 |
| 2003/0157039 A1 | 8/2003 | Ferrero et al. | |
| 2007/0073487 A1* | 3/2007 | Albright | G01J 1/02 702/3 |
| 2008/0194928 A1 | 8/2008 | Bandic et al. | |
| 2009/0138244 A1* | 5/2009 | Schuler | G06Q 10/04 703/2 |
| 2011/0191272 A1* | 8/2011 | McGuire | G01J 1/0219 706/11 |
| 2011/0247718 A1* | 10/2011 | Samain | B01F 15/00305 141/1 |
| 2011/0288680 A1* | 11/2011 | Samain | B01F 13/1055 700/239 |
| 2013/0262345 A1* | 10/2013 | Ciavarella | A47K 5/1208 705/500 |
| 2015/0338272 A1 | 11/2015 | Rastegar et al. | |
| 2018/0017437 A1 | 1/2018 | Poutiatine | |
| 2018/0192832 A1* | 7/2018 | Shaukat | A47K 5/1204 |

* cited by examiner

METHOD FOR AUTOMATICALLY SELECTING AND PROVIDING SUNSCREEN FOR USERS

CROSS-REFERENCE TO RELATED APPLICATIONS

This Application claims the benefit of U.S. Provisional Application No. 62/577,070, filed on 25 Oct. 2017, which is incorporated in its entirety by this reference.

This Application is a continuation-in-part application of U.S. patent application Ser. No. 15/926,282, filed on 20 Mar. 2018, which: claims the benefit of U.S. Provisional Application No. 62/473,937, filed on 20 Mar. 2017; claims the benefit of and U.S. Provisional Application No. 62/473,940, filed on 20 Mar. 2017; and which is a continuation-in-part application of U.S. Provisional application Ser. No. 15/648,158, filed on 12 Jul. 2017, each of which is incorporated in its entirety by this reference.

This Application is also a continuation-in-part application of U.S. patent application Ser. No. 15/648,158, filed on 12 Jul. 2017, which claims the benefit of U.S. Provisional Application No. 62/361,414, filed on 12 Jul. 2016, U.S. Provisional Application No. 62/380,455, filed on 28 Aug. 2016, U.S. Provisional Application No. 62/404,131, filed on 4 Oct. 2016, and U.S. Provisional Application No. 62/434,184, filed on 14 Dec. 2016, each of which is incorporated in its entirety by this reference.

TECHNICAL FIELD

This invention relates generally to the field of sunscreen and more specifically to a new and useful method for automatically selecting and providing sunscreen for users in the field of sunscreen.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
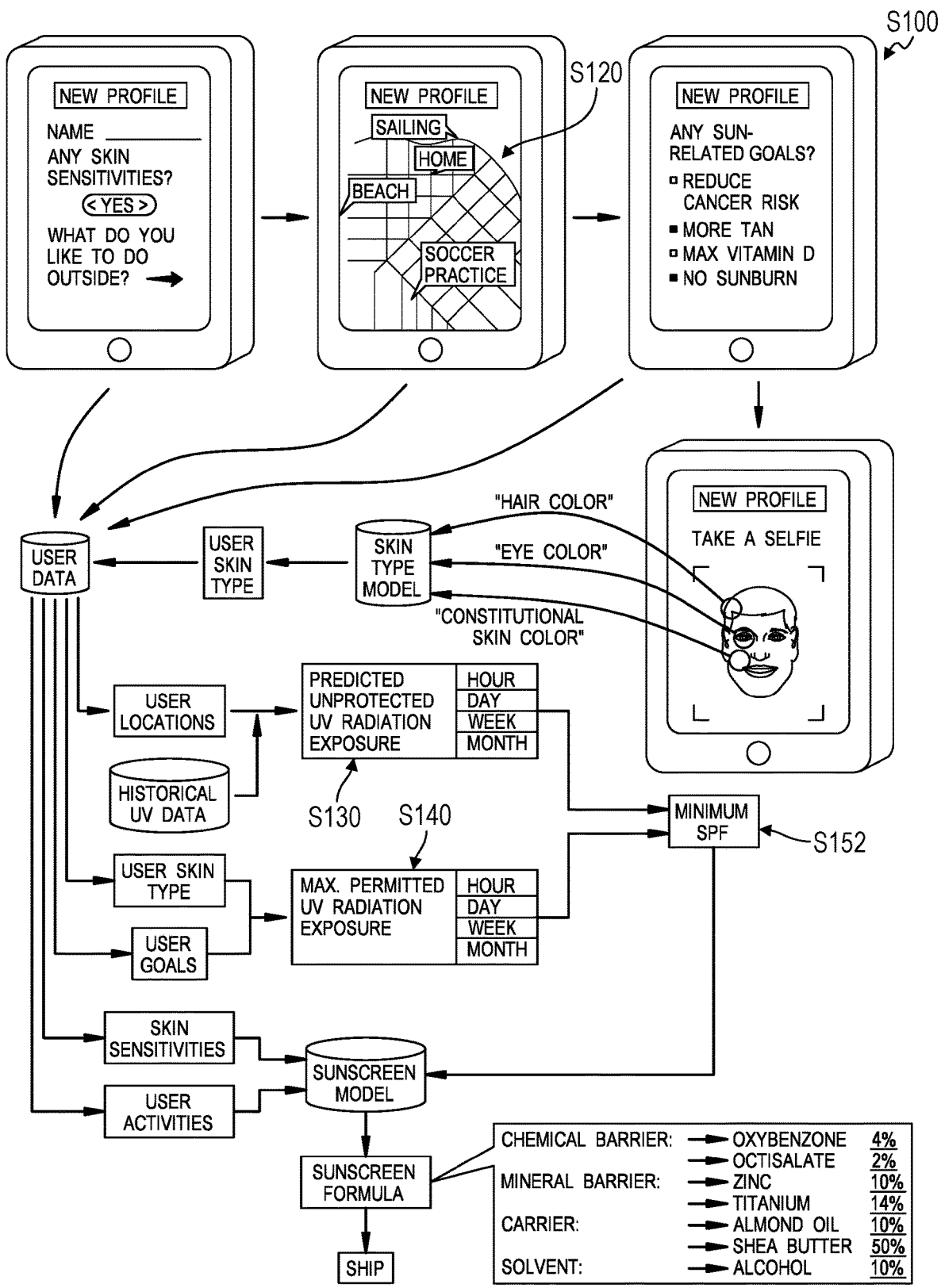
FIG. 1 is a flowchart representation of a method.
Figure 2:
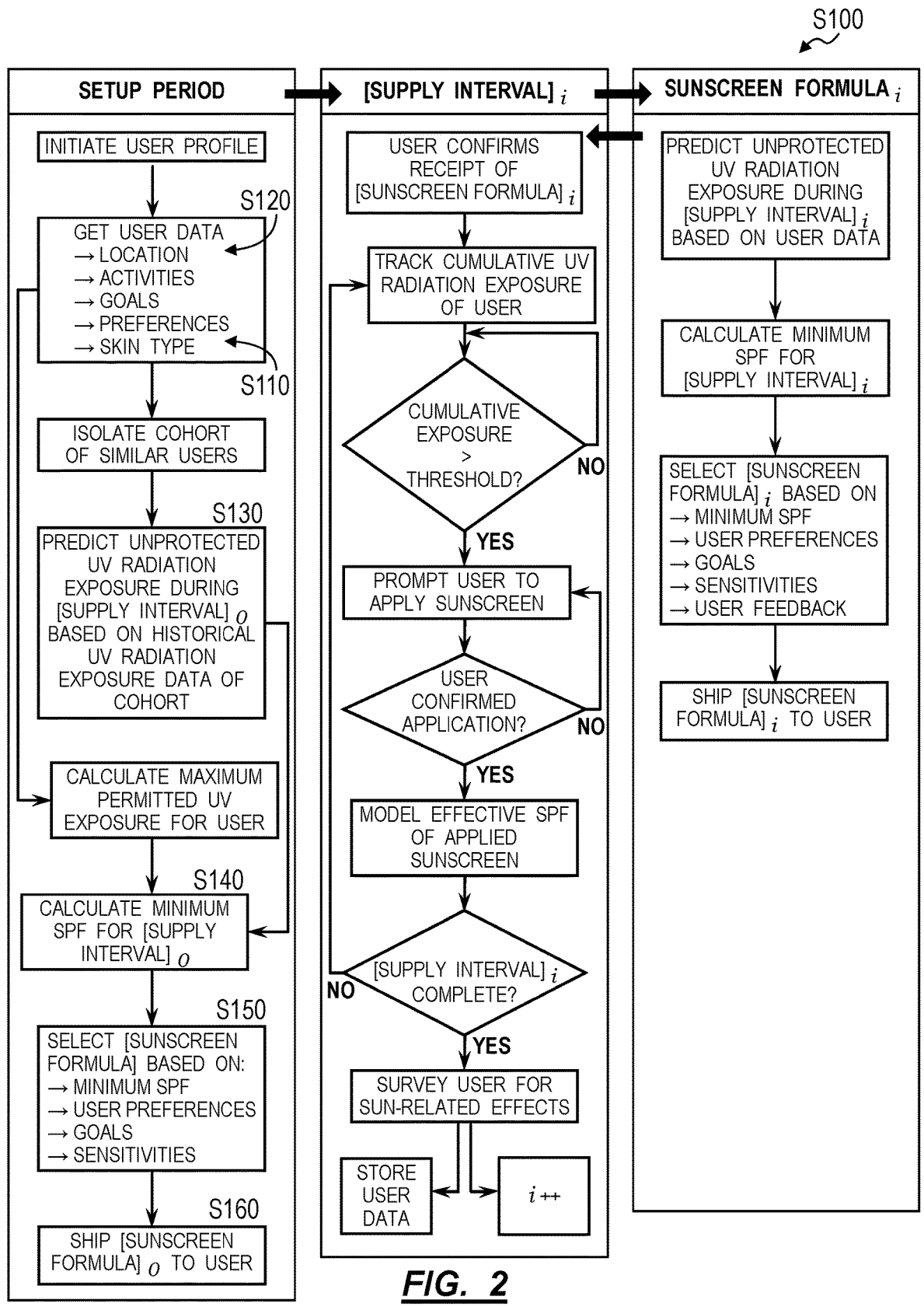
FIG. 2 is a schematic representation of a variation of the method.
Figure 3:
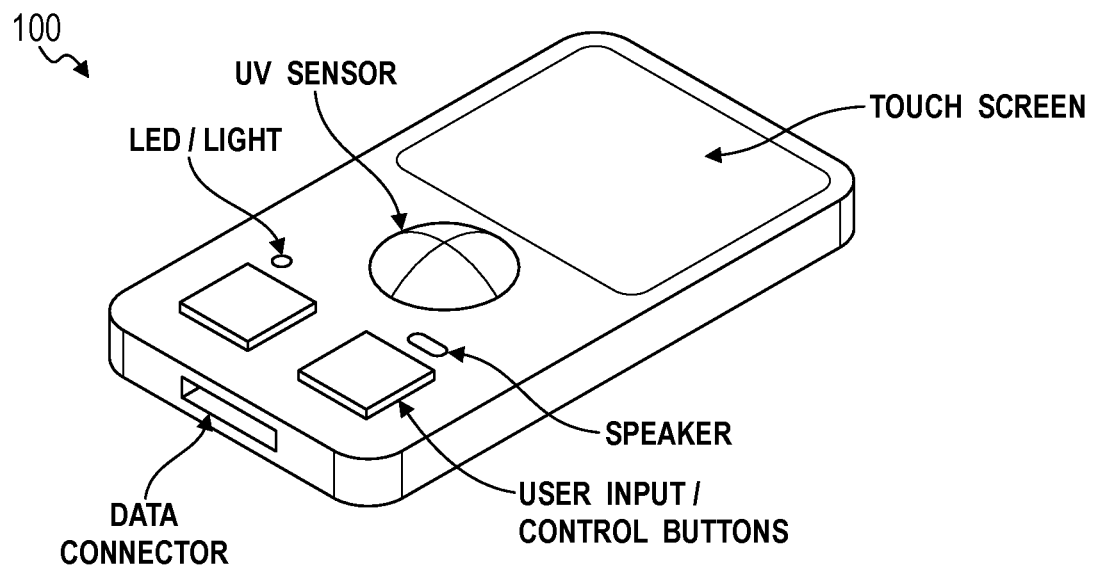
FIG. 3 is a graphical representation of a dispenser system.

As shown in FIGS. 1 and 2, a method S100 for automatically selecting and providing sunscreen for users includes: accessing a skin type of a user in Block S110; predicting a first set of locations occupied by the user during a first future supply interval in Block S120; based on historical ultraviolet irradiance data and the first future supply interval, calculating a first predicted unprotected ultraviolet radiation exposure of the user during the first future supply interval in Block S130; selecting a first sunscreen formula based on the first predicted unprotected ultraviolet radiation exposure and the skin type of the user in Block S150; and supplying a first volume of the first sunscreen formula to the user in Block S160.

One variation of the method S100 includes: accessing a skin type of a user in Block S110; predicting a first set of locations occupied by the user during a first future supply interval in Block S120; based on historical ultraviolet irradiance data and the first future supply interval, calculating a first predicted unprotected ultraviolet radiation exposure of the user during the first future supply interval in Block S130; calculating a maximum allowable ultraviolet radiation exposure for periods within the first future supply interval based on the skin type of the user in Block S140; calculating a first minimum sun protection factor predicted to reduce the first predicted unprotected ultraviolet radiation exposure to less than the maximum allowable ultraviolet radiation exposure in Block S152; selecting a first sunscreen formula characterized by a first sun protection factor greater than the first minimum sun protection factor in Block S150; and shipping the first volume of the first sunscreen formula to the user prior to the first future supply interval in Block S160.

2. Applications

Generally, the method S100 can be executed by a system: to generate a user profile for a new user; and to aggregate various characteristic data of the user, such as the user's age, the user's gender, the user's skin type, the user's sun-related health goals, the user's location and altitude, common outdoor activities performed by the user during specific times of year, how frequently the user applies sunscreen, the user's preference (e.g., for all-natural ingredients), the user's sensitivities (e.g., skin reactions and allergies), and/or medical conditions that may affect sun sensitivity. The system can then calculate a maximum allowable ultraviolet radiation exposure (hereinafter "UV exposure") for the user—such as on an hourly, daily, weekly, and/or monthly basis—based on the user's skin type and sun-related health goals; to predict the user's future ultraviolet exposure (e.g., ultraviolet-A, ultraviolet-B, and/or erythemal ultraviolet irradiance, ultraviolet index, or "UV index") based on the user's location and common outdoor activities and based on historical ultraviolet irradiance data for this location. The system can further execute Blocks of the method: to derive target characteristics (e.g., sun protection factor, or "SPF") of a sunscreen that, if worn by the user, may reduce the user's actual ultraviolet exposure to below the maximum allowable ultraviolet exposure, such as over hourly, daily, weekly, and/or monthly periods given the user's outdoor activities; to automatically select a particular sunscreen from a population of existing sunscreens or automatically generate a "custom" sunscreen formula or specification that fulfills these target characteristics; and to then supply (e.g., ship) a volume of this particular sunscreen or custom sunscreen formula—sufficient for a duration of an upcoming supply interval (e.g., one month)—to the user.

In particular, the system can execute Blocks of the method S100 to leverage historical sun-related georeferenced data, historical ultraviolet exposure data for various other users on a platform, atmospheric ultraviolet radiation models, and limited data characteristic of a new user on the platform: to predict the new user's unprotected ultraviolet exposure (e.g., ultraviolet-A, ultraviolet-B, or erythemal ultraviolet irradiance without use of sunscreen) during an upcoming supply interval (e.g., a one-month interval beginning at supply of a volume of a first sunscreen for the user); and to set a maximum allowable ultraviolet exposure for the user on an hourly, daily, weekly, or other interval within this upcoming supply interval, such as based on the user's skin type and health goals. The system can then: select or formulate a sunscreen that, if applied by the user during this upcoming supply interval, will limit her cumulative ultraviolet exposure to less than the maximum allowable ultraviolet exposure while also fulfilling the user's other preferences, goals, limitations related to the user's common activities (e.g., swimming or exercising outside), medical and sensitivity constraints, and external limitations (e.g., a coral-safe sunscreen requirement on a beach frequented by the user); and provide a volume of this sunscreen—sufficient for the duration of the upcoming supply interval—to the user, such as by shipping this volume of the sunscreen to the user in the mail.

The system can thus include a user portal—such as contained within a native application or accessed through a web browser executing on a user's computing device (e.g., smartphone, tablet, laptop computer)—configured to collect characteristics data from the user. The system can also include a remote computer system configured to access historical ultraviolet data from a database, to access atmospheric ultraviolet radiation models, to access characteristic data collected from the user at the user portal, to predict the user's future ultraviolet exposure and to set ultraviolet exposure limits for the user accordingly, and to select an existing sunscreen or to define a "custom" sunscreen formula or specification that fulfills these limitations. The system can further include a standalone ultraviolet sensor module: configured to detect intensity of incident ultraviolet radiation; configured to return incident ultraviolet radiation values to the user's computing device and/or to the remote computer system; and configured to be worn by a user (e.g., worn on a wrist strap, connected to an article of clothing or clipped on to a bag or backpack) or configured to couple to a sunscreen container (e.g., in the form of a sunscreen bottle lid). Alternatively, the user's computing device can include a ultraviolet sensor module, and the remote computer system can access incident ultraviolet radiation data collected by the user's computing device over time.

Thus, once the system provides a volume of sunscreen—selected specifically for the user based on the user's skin type and preferences and based on the predicted location and activities of the user during an upcoming supply interval—the system can track the actual ultraviolet exposure of the user via a standalone or integrated ultraviolet sensor module carried by the user, receive confirmation from the user that she has applied the sunscreen, and collect feedback from the user, such as regarding whether the user has experienced a sunburn. The system can later combine these data with user location, user activity, and historical ultraviolet data to predict sunscreen needs, to select a second sunscreen (or define a second "custom" sunscreen formula or specification) for the user for a next supply interval, and to supply the user with this second sunscreen accordingly prior to this next supply interval.

The system can therefore execute Blocks of the method S100 to: select a first sunscreen for a user for the user's first supply interval based on limited user data (e.g., by relying on historical data from other, similar users) once the user is added to a platform; collect sunscreen- and ultraviolet exposure-related data from the user over time; and leverage these additional user data to select other sunscreens for the user for subsequent supply intervals, thereby compensating for both user actions, activities, needs, and preferences of the user and changing environmental conditions around the user over time.

For example, the system can initially access user characteristics—such as location, skin type, sunscreen-related preferences, time spent during this time of year performing outdoor activities, short-term sun-related needs, and long-term health goals—via the user portal executing on the user's computing device. The system can then: match the user to one sunscreen in a population of existing sunscreen formulas or generate a custom sunscreen formula or specification for the user based on these user characteristics; and send a volume (e.g., 4 ounces) of this sunscreen formula to the user. Once the user has this sunscreen in hand, the system can serve sunscreen-related prompts and guidance to the user, such as when, how much, and how frequently to apply this sunscreen based on the user's location and/or based on the local time of day, or the incident ultraviolet radiation data collected by the user's computing device or affiliated ultraviolet sensor module. The system can repeat this process to match the user to a particular sunscreen formula on a fixed interval (e.g., biweekly, monthly, seasonally) or on a variable interval (e.g., as a current bottle of sunscreen supplied to the user approaches empty, as indicated manually by the user or detected via a sensor integrated into or connected to the bottle). The system can implement similar methods and techniques to select an existing sunscreen or generate a new sunscreen formula for the user responsive to a request for sunscreen from the user, such as in preparation for the user leaving for a trip.

The method S100 is described below as executed by the system to select or define a sunscreen formula for a user based on various user characteristic, user location, and/or user activity data. However, the system can additionally or alternatively execute Blocks of the method to select or define other skin and sun-related products for the user, such as: pre-sun products (e.g., vitamin-C serums to add antioxidants to a user's skin) moisturizers exhibiting sun protection properties; anti-aging serums exhibiting sun protection properties; makeup products exhibiting sun protection properties; and/or after-sun products, such as to treat a sunburn or to help a user's skin to heal.

3. System

As described above, Blocks of the method S100 can be executed by a system that includes: a user portal accessible via a computing device; a remote computer system configured to collect user and ultraviolet exposure data for a population of users and to select sunscreens for users based on these data; a ultraviolet sensor module integrated into a standalone mobile device or into a user's mobile computing device; and a sunscreen distributor configured to warehouse, mix, and/or ship volumes of sunscreen (e.g., in bottle format) to users on the platform.

3.1 User Portal

The user portal can be accessed by a user via a native application or web browser executing on the user's computing device (e.g., a smartphone, a tablet) in order to: create a new user profile; enter demographic information; indicate common outdoor activities and durations of these activities performed by the user at various locations in the past and/or planned for the future; indicate sunscreen preferences; enter health- and sun-related goals; indicate a scheduled location change (e.g., for a beach vacation, a skiing vacation); etc.

3.2 Remote Computer System

The remote computer system can include a computer network or remote server, etc. and can access or include a database configured to store historical ultraviolet data for a geographic region, a mathematical model to predict ultraviolet radiation levels at specific dates and times that includes atmospheric and altitude effects, user profile data, user ultraviolet exposure data, and user feedback for a population of users on the platform. For example, the remote computer system can: access database mathematical ultraviolet radiation model; access user profile data and sunscreen application feedback entered by a user via an instance of the user portal executing on the user's mobile computing device; access user location and activity data from the user's mobile computing device; and access ultraviolet irradiance data collected by the user's mobile computing device and/or by a standalone ultraviolet sensor module carried or worn by the user.

3.3 UV sensor module and Mobile Computing Device

The ultraviolet sensor module can define a standalone ultraviolet-tracking device, such as configured to: clip on to a bag or backpack (e.g., described in U.S. patent application Ser. No. 15/648,158); connect to an article of clothing (e.g., described in U.S. patent application Ser. No. 15/926,282); or attach to a sunscreen bottle (e.g., in the form of a cap, lid, or sleeve for a sunscreen bottle). The ultraviolet sensor module can then implement methods and techniques described below to record intensities of incident ultraviolet radiation; and the ultraviolet sensor module, the user's mobile computing device, and/or the remote computer system can then implement methods and techniques described below to transform these incident ultraviolet radiation into local ultraviolet indices and to estimate the user's ultraviolet exposure accordingly over time.

3.3.1 UV Sensor Module Components

In one implementation, the ultraviolet sensor module includes: a housing, such as a plastic injection-molded and thermoplastic elastomer (TPE) over-molded housing; an ultraviolet radiation sensor, such as a digital ultraviolet irradiance photodiode light sensor or other optical ultraviolet radiation sensor, adjacent a ultraviolet-transparent region of an outer surface of the housing; memory arranged in the housing; a controller arranged in the housing and configured to sample the ultraviolet radiation sensor and other sensors housed within the ultraviolet sensor module and to store incident solar radiation data to memory; a wireless communication module arranged in the housing and configured to receive location data from a local mobile computing device and transmit solar radiation data to a local mobile computing device, such as in real-time, intermittently (e.g., one per three-minute interval), or asynchronously (e.g., after establishing a wireless connection between the user's mobile computing device and the ultraviolet sensor module); and a rechargeable battery arranged in the housing configured to power the controller, sensors, and the wireless communication model.

The ultraviolet sensor module can also include motion and orientation sensors configured to record pitch, yaw, and roll orientations of the ultraviolet sensor module, such as relative to the reference frame of the Earth or to an arbitrarily-defined reference frame. Thus, the ultraviolet sensor module can also include an accelerometer or tilt sensor configured to detect pitch and roll orientations of the ultraviolet sensor module; a compass sensor configured to detect yaw orientation of the ultraviolet sensor module; and a gyro sensor or angular velocity sensor configured to detect a rate of angular pitch, roll, and yaw motion. In one implementation, the controller can thus transition from an inactive (e.g., "sleep" or "hibernate") low power mode to an active mode responsive to an output of the motion sensor and/or predict an activity of the user wearing the exposure-tracking module based on a magnitude and/or frequency of outputs of the motion and orientation sensors.

The ultraviolet sensor module also includes an ultraviolet radiation sensor configured to output a signal proportional to incident ultraviolet radiation. In one example, the ultraviolet radiation sensor is broadly sensitive to ultraviolet radiation and includes an ultraviolet filter configured to pass ultraviolet radiation within a limited erythemal action spectrum and to reject ultraviolet light outside of this spectrum. The ultraviolet radiation sensor can thus define an erythemally-filtered ultraviolet radiation sensor. In this example, the ultraviolet filter can pass ultraviolet-B (which may not pass through glass) but reject ultraviolet-A (which may pass through glass); thus when the ultraviolet sensor module detects ambient light at the ambient light sensor but no ultraviolet radiation at the ultraviolet radiation sensor, the ultraviolet sensor module can determine that it is occupying an indoor space. However, because ultraviolet-A exposure may be proportional to ultraviolet-B exposure when outdoors, the ultraviolet sensor module can predict both ultraviolet-A and ultraviolet-B exposure of a user based on degree of ultraviolet-B radiation detected at the ultraviolet radiation sensor.

In the foregoing example, the filter can also be polarized in order to selectively pass ultraviolet radiation within a narrow range of incident angles (e.g., normal to the ultraviolet radiation sensor ±5°) in order to increase sensitivity of a signal output by the ultraviolet radiation sensor to its orientation. The ultraviolet radiation sensor can additionally or alternatively include a diffuser that functions to accommodate angular misalignment of the ultraviolet sensor module from a target orientation by funneling ultraviolet radiation over a wider angular window into a sensing element in the ultraviolet radiation sensor. However, the ultraviolet sensor module can include any other type and/or quantity of ultraviolet radiation sensor (e.g., a UVA sensor), visible light sensor, and/or infrared radiation sensor.

Additionally or alternatively, the ultraviolet sensor module can include additional sensors, such as an ambient temperature sensor, a humidity sensor, a heart-rate monitoring sensor, a skin temperature sensor, an infrared (IR) irradiance sensor, a visible light irradiance sensor, an altimeter, a barometer, a moisture or water exposure sensor, any other ambient condition sensor configured to record parameters of ambient conditions surrounding the ultraviolet sensor module, and/or any other biometric sensor configured to record biometric parameters of a user associated with the ultraviolet sensor module.

The ultraviolet sensor module can also include a wireless communication module configured to receive date, time, and location data from the user's mobile computing device and/or to push ultraviolet radiation-related and or exposure-related data back to the user's mobile computing device.

3.3.2 Data Collection and Ultraviolet Irradiance Processing

In one implementation, orientation sensors (e.g., a multi-axis gyroscope, compass, accelerometer, and/or tilt sensor) integrated into the light exposure device can output yaw, pitch, and roll orientations of the light exposure device, such as relative to the reference frame of the Earth or relative to an arbitrarily-defined reference frame. For example, the light exposure device can include a compass sensor, a multi-axis tilt sensor or accelerometer, and a multi-axis gyroscopic sensor; and the light exposure device can fuse an absolute compass direction output by the compass, angular velocity values output by the gyroscopic sensor, and acceleration values output by the tilt sensor or accelerometer into a pitch, yaw, and roll position of the light exposure device relative an Earth reference frame per sampling interval. From the solar position, the light exposure device can define a target direct orientation for the light exposure device, such that, when outputs of these sensors indicate that the light exposure device is aligned with the target direct orientation, a ultraviolet sensor integrated into the light exposure device is directed orthogonal the Sun.

In particular, rather than prompting a user wearing (or carrying) the light exposure device to manually align the light exposure device with the target direct orientation during a sampling interval, the light exposure device can: intermittently wake from a sleep state to collect ultraviolet data (e.g., once per fifteen-minute interval); define target direct, diffuse, and/or global orientations for collection of ultraviolet values during this interval; regularly sample the orientation sensors during this interval to monitor the orientation of the light exposure device; automatically record ultraviolet values from the ultraviolet sensor in response to the orientation of the light exposure device falling within a threshold difference from each of the target direct orientation, the target diffuse orientation, and/or the global orientation; transform these ultraviolet values into a ultraviolet exposure value for the user for this interval; and then return to the sleep state. The light exposure device can repeat this cycle over time, such as during known daylight hours for the current date and location of the light exposure device, and aggregate ultraviolet exposure values for each interval during a single day into a cumulative ultraviolet exposure value for the user for this day.

For example, the user may rotate the light exposure device into the target global orientation while opening a door or performing any other task; in response to detecting that its orientation has fallen within a threshold difference of the target direct orientation (or a range of direct orientations) for the current time of day, date, and approximate geolocation of the light exposure device, the light exposure device can record a global ultraviolet value. The light exposure device can similarly record ultraviolet values when the detected orientation of the light exposure device falls within threshold differences of the target direct and diffuse orientations. (However, the light exposure device can opportunistically collect ultraviolet data for other target orientations of the light exposure device based on predicted positions of the Sun relative to Earth at corresponding times of day, days of the year, and locations stored on the light exposure device.)

As shown in FIG. 2, the light exposure device can also include an ambient light sensor configured to output a signal corresponding to a level of incident ambient (visible) light and arranged proximal the ultraviolet sensor in the light exposure device. For example, in response to lack of a signal from the ambient light sensor during known daylight hours at the current time and location of the light exposure device, the light exposure device can determine that the ambient light sensor is obscured, such as by a sleeve covering a wrist on which the light exposure device is worn by a user. Because the ambient light sensor is adjacent the ultraviolet sensor, obfuscation of the ambient light sensor may indicate similar obstruction of the ultraviolet sensor. Therefore, the light exposure device can postpone or cancel collection of ultraviolet data during a current sampling interval while the ambient light sensor is obstructed, thereby avoiding recordation of aberrant or irrelevant ultraviolet values when conditions surrounding the ultraviolet sensor are unfavorable to collection of accurate sensor data.

In the foregoing example, the light exposure device can also detect presence of ambient light based on an output of the ambient light sensor, confirm that the ambient light and ultraviolet sensors are not obscured, and then enable collection of ultraviolet data through the ultraviolet sensor. (Similarly, the light exposure device can concurrently sample the ambient light sensor and the ultraviolet sensor when the light exposure device aligns with a target orientation and then retroactively confirm that the ultraviolet sensor was not obscured during this sampling interval based on an ambient light level read from the ambient light sensor during this same sampling interval.) However, in response to detecting the presence of ambient light but little or no ultraviolet radiation (e.g., UVB specifically, which may penetrate fused silica and fused quartz but may not penetrate other common glasses), the light exposure device can determine that it is located indoors and estimate the user's ultraviolet exposure at null until an increase in detected incident ultraviolet radiation—indicating that the light exposure device is outdoors—is recorded.

Furthermore, the ambient light sensor can cooperate with the ultraviolet sensor to prioritize target orientations for recording ultraviolet values. For example, in response to detecting the presence of ambient light, the light exposure device can record a direct ultraviolet value in response to detecting its alignment with the target direct orientation, a diffuse ultraviolet value in response to detecting its alignment with the target diffuse orientation, and a global ultraviolet value in response to detecting its alignment with the target global orientation. In this example, the light exposure device can determine that the direct ultraviolet value corresponds to an ultraviolet irradiance significantly less than ultraviolet indices corresponding to the global and diffuse ultraviolet values. Thus, the light exposure device can determine that its location is outside yet away from direct sunlight, such as in a shaded area or under overcast skies, and can temporarily reject direct ultraviolet values recorded by the ultraviolet sensor, thereby applying the direct and diffuse ultraviolet values to calculate a current ultraviolet irradiance based on shade or cloudy sky ultraviolet exposure models and algorithms.

3.3.3 Integrated Ultraviolet Sensor Module

Alternatively, the ultraviolet sensor module can be integrated directly into the user's mobile computing device, and an instance of the user portal or the remote computer system can implement methods and techniques described above to transform incident ultraviolet radiation data read by the ultraviolet sensor module—in the user's mobile computing device—into local ultraviolet indices and estimate the user's ultraviolet exposure accordingly over time.

4. Data for Sunscreen Selection or Formulation

In preparation for selection of a first sunscreen formula for an upcoming supply interval for a new user, the system can interface with the user—via the user portal—to collect user profile data, such as the user's skin type, sunscreen-related preferences, and location and to identify time spent by the user performing various outdoor activities at various locations in the past and/or anticipated time spent by the user performing various outdoor activities during the upcoming supply interval, as shown in FIG. 1.

4.1 User Characteristics

In one implementation, when the user initiates a new user profile on the platform, the user portal can query the user to enter or supply information related to her skin type, demographic information (e.g., age, gender, occupation), and skin sensitivities.

For example, the user's skin type may indicate a rate of skin damage in the presence of ultraviolet radiation (or "sunburn"). In this example: a skin type on a first end of a skin type spectrum (e.g., white skin color, or a Fitzpatrick skin type value of "1") may be correlated with frequent, rapid sun-burning with nearly null probability of tanning; a skin type proximal a center of the Fitzpatrick skin type spectrum (e.g., light brown skin color, or a skin type value of "3") may exhibit mild burn on occasion and may tan uniformly; and a skin type proximal a second end of this skin type spectrum (e.g., darkest brown skin color, or a Fitzpatrick skin type value of "6") may never burn but may be prone to hyper-pigmentation. The system can therefore collect the user's skin type from the user and leverage this information to predict the user's probability of developing a sunburn and probability of developing a tan and then select a (minimum) SPF value for the next supply interval for the user accordingly.

In another example, humans may exhibit greater sensitivity to ultraviolet radiation (e.g., exhibit greater probability of developing sunburn) and may exhibit longer recovery times following sunburn with increasing age. The system can therefore select a higher SPF value for the upcoming supply interval for the user responsive to a greater age of the user in order to reduce likelihood of the user developing a sunburn while wearing a sunscreen supplied by the system; and vice versa.

Furthermore, the user may exhibit a particular skin sensitivity or have skin that is generally sensitive, such as due to a medical condition (e.g., Lupus). If the user confirms sensitive skin via the user portal, the system can thus select sunscreen formulas that contain physical ultraviolet barriers only (i.e., that exclude chemical barriers, such as oxybenzone and octinoxate). In a similar example, for a user who suffers from melasma and who may experience hyper-pigmentation when exposed to ultraviolet radiation or heat, the system can select sunscreen formulas containing high proportions of mineral barriers (e.g., zinc-oxide and/or titanium-dioxide) that reflect—rather than absorb—incident ultraviolet radiation in order to both protect the user's skin from UV radiation and radiation heating.

However, the system can query the user for any other user characteristic information and can store these data in a user profile associated with the user.

4.1.1 Skin Type

In one implementation, the user portal presents a set of questions related to eye color, hair color, ethnic group, skin color, presence of freckles, and/or tanning ability, etc. Based on responses entered by the user, the system can predict the user's skin type in Block S110. In another implementation, the user portal: presents a set of images of humans of different skin types; prompts the user to select a subset of images best depicting the user's skin, eye, hair, and ethnic features; and then predicts the user's skin type in Block S110 based on the user's responses.

In yet another implementation shown in FIG. 1, the user portal serves a prompt to the user to record a digital photographic image of the user's face with the user's mobile computing device. The remote computer system (or the user portal) then: accesses this digital photographic image; implements face detection techniques to detect a region of the photographic image depicting a face; and then implements object recognition or other computer vision techniques to extract an eye color, a hair color, a constitutional skin color, and/or a proportion of pigment cell clusters (e.g., "freckles") from the region of the photographic image. The remote computer system can then calculate the skin type of the user (e.g., in the form of a qualitative or quantitative value) in Block S110 based on the eye color, the hair color, the constitutional skin color, and the proportion of pigment cell clusters extracted from the region of the photographic image. For example, in this implementation, the system can interface with the user via the user portal to record an image of the user's face, implement computer vision techniques to detect the user's face in the image and to extract various facial features from the image (e.g., eye color, constitutional skin color, hair color, freckle distribution), and then implement a Fitzpatrick skin type model to transform these facial features into a skin type, such as one of a set of (e.g., six) predefined skin types or a quantitative skin type value along a continuous spectrum of skin types.

In the foregoing implementation, the system can additionally or alternatively implement similar methods and techniques to: record digital photographic images of other regions of the user's body, such as one image of her shoulder and another image of her forearm; extract features from these images; and derive the user's skin type based on a combination of these features and/or combine this information with user-supplied skin tanning behavior information.

However, the system can implement any other method or technique to derive or estimate the user's skin type.

4.2 User Location

Block S120 of the method S100 recites predicting a first set of locations occupied by the user during a first future supply interval. Generally, in Block S120, the system can access one or a set of locations characteristically occupied by the user, such as: a singular common location occupied most frequently by the user (e.g., the location of the user's main home or vacation property in which the user is currently residing); multiple discrete locations in which the user spends a large proportion of her time (e.g., locations of the user's home, office, and primary pastime location); or a time series of locations occupied by the user on a characteristic day (e.g., a characteristic weekday or weekend day). The system can then leverage these user location data, historical georeferenced ultraviolet irradiance data, mathematical atmospheric ultraviolet radiation models, and/or historical ultraviolet exposure data of other users on the platform who have frequented these locations to predict the user's unprotected ultraviolet exposure—such as on hourly or daily bases—during an upcoming supply interval, as described below. In a similar manner, the system can access a current user location (e.g., through GPS, cellular networks, etc.), and leverage this user location data, alone or in combination with other past, present or future location data, historical georeferenced ultraviolet irradiance data, mathematical atmospheric ultraviolet radiation models, and/or historical ultraviolet exposure data of other users on the platform who have frequented these locations to predict the user's unprotected ultraviolet exposure—such as on hourly or daily bases—during an upcoming supply interval, as described below. The system can also leverage these user location data to predict external sunscreen limitations, such as coral-safe requirements and/or location-specific chemical limitations.

In one implementation, the system: accesses a geospatial location of the user's mobile computing device during initial setup of a user profile for the user; and then prompts the user to either confirm this location as her "home" location or enter an alternate home location. (The system can alternatively prompt the user to indicate a geospatial location in which she spends the greatest proportion of her time per week, such as by dropping a "pin" onto a geospatial map rendered within the user portal.) In a similar implementation, the system can prompt the user to draw a boundary—on a virtual map depicted within the user portal—around a geospatial region in which she spends most of her time.

The system can additionally or alternatively prompt the user to indicate (e.g., by annotating a map depicted within the user portal) locations that the user commonly occupies, such as: her home; her office or current work location; and the location of her common outdoor activities, such as locations of a garden (e.g., for gardening), an outdoor pool (e.g., for swimming), a field or stadium (e.g., for playing soccer or watching football), a bike path, a walking path (e.g., for walking a dog), and/or a lake (e.g., for fishing), etc. For example, the system can prompt the user to: drop a pin—on a map depicted within the user portal—at each of these locations; label each pin with its type and/or activity commonly performed by the user at this location (e.g., by selecting the pin and linking the pin to an activity selected in a dropdown menu within the user portal); and/or label this pin with typical days of the week on which the user occupies the corresponding location, the user's typical arrival time, and the user's typical departure time for this corresponding location.

In another example, during initial setup of a user profile for the user, the system can: serve a survey to the user for a set of outdoor activities and durations of time that the user commonly spends performing these activities during the current time of year; prompt the user to select relevant outdoor activities (e.g., working outside, gardening, swimming, cycling, running, barbecuing, kayaking, playing tennis, etc.) from a dropdown menu or to check relevant activities from a prepopulated list of outdoor activities; prompt the user to indicate a typical amount of time spent by the user on a daily, weekly, or other basis performing each of these indicated outdoor activities; and prompt the user to indicate times of day that the user typically performs these activities. The system can also prompt the user to enter a city, zip code, or specific address in which the user performs each of these indicated outdoor activities or otherwise confirm that she performs these outdoor activities within a current city or other geographic region currently occupied by the user. Therefore, in this implementation, the system can query the user for a set of outdoor activities commonly performed by the user during the current time of year.

Additionally or alternatively, rather than prompt the user to indicate locations she commonly occupies and outdoor activities she performs at these locations, the system can prompt the user to indicate locations, activity types, and durations of activities that the user has planned or anticipates performing during the upcoming supply interval, such as by populating a weekday schedule and weekend schedule with characteristic activities anticipated by the user for the upcoming supply interval.

In another implementation, the system accesses historical geospatial location data of the user's mobile computing device, such as geospatial locations recorded on minute- or hourly-intervals by the user's mobile computing device over time. For example, the system can retrieve timestamped geospatial data from the user's mobile computing device and then compile these data into a heatmap of historical locations occupied by the user. The system can then extrapolate these location data forward into the upcoming supply interval to predict a particular predominate location, multiple predominate locations, a time series of locations, or a heatmap of locations, etc. that the user will occupy throughout the upcoming supply interval.

In another implementation, the system can: access a digital calendar associated with the user, such as from the user's mobile computing device or from a separate online calendar; and extract a set of locations and a corresponding set of outdoor activities from a set of events contained in the digital calendar (e.g., spanning the upcoming supply interval). In particular, the system can: prompt the user to enable access to her calendar; scan calendar events within the user's calendar; extract addresses or locations and activity types from calendar events within the user's calendar, such as times and locations of a planned bike ride, a planned beach trip, a planned skiing trip, or a planned baseball game; and then compile these locations and activity types into a heatmap of future locations and activities planned by the user. (Additionally or alternatively, the system can similarly scan past calendar events, extract locations and durations of various activities from past events noted in the user's calendar, and then extrapolate locations and durations of such activities performed by the user during the upcoming supply interval.)

However, in the foregoing implementations, the system can implement any other method or technique to collect past, current, and/or predicted future location and activity data for the user and/or to extrapolate future locations and activities of the user based on historical user location and activity data.

In one implementation, the system then leverages the foregoing location and activity data to construct a virtual map (e.g., a geospatial heatmap) or a time series of locations that the user is predicted to occupy during the upcoming supply interval. The system can further filter this virtual map or time series to include only locations in which the user performs outdoor activities (e.g., gardening, fishing, cycling, playing baseball). However, the system can construct any other representation of predicted and/or scheduled outdoor activities of the user during the upcoming supply interval based on activity and location data supplied by the user.

The system can store these activity and location data in the user's profile and later leverage these data to: predict times that the user will be outside; predict the user's geospatial locations when outside; retrieve ultraviolet irradiance data for these locations; and integrate ultraviolet irradiance data for these outdoor locations over predicted times that the user will occupy these outdoor locations to estimate the user's unprotected ultraviolet exposure, such as on hourly, daily, and/or weekly bases. The system can then select a sunscreen formula or specification for the user accordingly, as described below.

Furthermore, once the user's profile has been added to the platform and once the user has received a first sunscreen formula selected by the system, the system can: track the user's location directly through the user's mobile computing device; track the user's ultraviolet exposure directly through an integrated ultraviolet sensor or through a standalone ultraviolet sensor module supplied to the user (e.g., by the system concurrently with the first sunscreen formula); and then leverage these user-specific data to predict the user's locations and unprotected ultraviolet exposure during a subsequent future supply interval, as described below.

4.3 User Sunscreen Preferences and Habits

The system can also prompt the user to indicate her sunscreen-related preferences, such as preferences for: all-natural sunscreens; hormone-free sunscreens; coral-safe sunscreens; zinc-free sunscreens; water resistant sunscreens; anti-aging sunscreens; etc. Later, the system can leverage these preferences to select a sunscreen formula that fulfills both the user's needs and preferences.

Similarly, the system can prompt the user to indicate her sunscreen-related habits. For example, the system can prompt the user to indicate when she typically applies sunscreen, such as selected from a pre-populated or reactive list including: daily (e.g., "during my morning routine"); whenever the user goes outside; before extended periods of outdoor activity; before and throughout extended periods of outdoor activity; before an athletic workout; after a minimum duration (e.g., twenty minutes) of outdoor activity; during extended periods of outdoor activity when the Sun is especially bright; upon arriving at a beach; or never; etc. Later, the system can leverage these preferences to select a sunscreen formula or specification characterized by sun protection factors, broad spectrum ultraviolet protection, water resistance, etc., that compensates for the user's sunscreen application habits (e.g., lower sun protection factors if the user regularly applies and reapplies sunscreen; higher sun protection factors if the user typically only applies sunscreen after an extended period of time in the Sun; lower sun protection factors if the user is at a high latitude; higher sun protection factors during summer).

(Generally, sun protection factor (or "SPF") described herein represents a measure of effectiveness of a sunscreen: in the UVB electromagnetic radiation wavelength band (e.g., approximately 280 nanometers to 320 nanometers); and/or in the UVA electromagnetic radiation wavelength band (e.g., 320 nanometers to 400 nanometers, or "protection factor UVA").)

Furthermore, once the user's profile has been added to the platform and once the user has received a first bottle of the first sunscreen formula selected by the system, the system can: track the user's application of the first sunscreen formula, such as indicated manually by the user via the user portal or detected via the ultraviolet sensor module or other sensor module coupled to the first bottle of the first sunscreen formula; and then derive the user's sunscreen application habits directly from these user data accordingly.

4.4 User Goals

During initial setup of the user profile for the user, the system can also serve a prompt, to the user, to select a sun-related goal, as shown in FIG. 1. For example, the system can prompt the user to select a particular goal or rank goals in a set of sun-related goals, such as including: "reducing long-term skin cancer risk"; "preventing sun burn"; "maintaining proper vitamin-D levels"; "preventing skin aging;" "increasing tan"; "maintaining tan"; and "reducing tan"; etc. In this example, if the user ranks "reducing long-term skin cancer risk" first, followed by "preventing sun burn," the system can: set high minimum UVA and UVB sun protection factors for the user; and then select or define a first sunscreen formula characterized by sun protection factors greater than—even significantly greater than—the minimum sun protection factor. However, if the user ranks "maintaining proper vitamin-D levels" first, followed by "maintaining tan," the system can: instead define a lower band of UVA and UVB sun protection factors for the user based on the user's predicted ultraviolet exposure during the upcoming supply interval and based on the user's age in order to balance the user's tan (produced by UVA exposure) and maintain high vitamin-D levels (produced by UVB exposure) (e.g., without additional vitamin-D supplements); and then select or define a first sunscreen formula or specification characterized by UVA and UVB sun protection factors that fall near these sun protection factors.

However, the system can collect any other data from the user during initial setup of the user's profile.

5. Predicted User Ultraviolet Exposure

Block S130 of the method S100 recites, based on historical UV radiation data (e.g., represented in a mathematical atmospheric ultraviolet radiation model), and the first future supply interval, calculating a first predicted unprotected ultraviolet exposure of the user during the first future supply interval. Generally, in Block S130, the system can calculate a predicted unprotected ultraviolet exposure of the user (i.e., the user's ultraviolet exposure if the user fails to wear sunscreen) based on predicted durations of time spent by the user at locations associated with activities that the user is predicted to perform during the upcoming supply interval. For example, the system can leverage historical georeferenced ultraviolet irradiance data, user location data, and user activity data, and predicted ultraviolet radiation levels, etc. to predict the user's unprotected ultraviolet exposure during the upcoming supply interval, such as broken into: one-hour intervals; four-hour intervals; daily intervals; weekly intervals; or two-week intervals; etc. within the upcoming supply interval. (Alternatively, the system can leverage a mathematical atmospheric ultraviolet radiation model constructed based on fundamental physics and geometries with empirically-determined atmospheric filtering in order to predict the user's unprotected ultraviolet exposure during the upcoming supply interval.)

5.1 Historical and Modeled Ultraviolet Irradiance Data

In one implementation shown in FIG. 1, once the user first completes her user profile on the platform, the system can: leverage historical ultraviolet irradiance data (e.g., collected from weather stations and/or ultraviolet sensor modules carried by other users on the platform) and ultraviolet radiation forecasts (e.g., derived from mathematical atmospheric ultraviolet radiation models) to predict ultraviolet indices at outdoor locations that the user is predicted to occupy during the upcoming supply interval; integrate these historical and forecast ultraviolet indices over periods of time that the user is predicted or scheduled to occupy these locations in order to estimate the user's unprotected ultraviolet exposure over periods of time at these locations during the upcoming supply interval; and then combine these periodic unprotected ultraviolet exposures to predict cumulative unprotected ultraviolet exposure on hourly, daily, weekly, or other bases during the upcoming supply interval.

In a similar implementation, the system accesses a time series of ultraviolet irradiance data within the user's geographic region over a one-month period preceding the upcoming supply interval by one year (i.e., ultraviolet irradiance data for the geographic region for the preceding year). The system also predicts the user's exposed skin area during periods of outdoor activity based on types of these activities and time of year, such as: only face exposed for snow sport activities; head, neck, arms, and legs for gardening-related activities; head, neck, and arms for landscaping and construction-related activities; head, neck, torso, arms, and legs for swimming- and beach-related activities; head, neck, arms, and legs for tennis, soccer, cycling, and running activities; arms and face for football activities; etc. The system can then: integrate this time series of ultraviolet radiation indices over the upcoming supply interval based on times of day, durations, and anticipated exposed skin area of predicted user activities during the upcoming supply interval in order to calculate a predicted unprotected ultraviolet exposure of the user. (The system can further segment this predicted unprotected ultraviolet exposure by hour, day, week, or other time interval, as described above.)

In another implementation, the system: accesses a time-series of historical ultraviolet irradiance data within the user's geographic region over a period of time (e.g., one month) preceding the upcoming supply interval by one year (i.e., ultraviolet irradiance data for the geographic region for the preceding year); and modifies a mathematical atmospheric ultraviolet irradiance model based on this location-specific historical ultraviolet irradiance data in order to improve the accuracy of the mathematical atmospheric ultraviolet irradiance for the user's geospatial location. For example, the system can modify this mathematical atmospheric ultraviolet irradiance in order to generate more accurate ultraviolet exposure predictions for a particular location that is typically foggy during a particular time of year.

In another (simplified) implementation, the system: accesses the historical ultraviolet irradiance data for a geographic region containing the user's predominant geospatial location; and then integrates these ultraviolet radiation indices over periods of time that the user is predicted to spend outside on an hourly, daily, weekly, or other basis during the upcoming supply interval, such as based types and locations of common outdoor activities indicated by the user in a survey described above.

5.2 Historical Ultraviolet Exposure Data

In one variation shown in FIG. 2, the system leverages historical ultraviolet exposure data of other users on the platform to predict the user's unprotected ultraviolet exposure during the upcoming supply interval.

In one implementation, the system: collects demographic information from the user, the user's primary location, and the user's preferred outdoor activities; and identifies a cohort of other users—on the sunscreen supply platform—who exhibit demographics (e.g., age, gender, skin type, occupation, etc.) similar to demographics of the user, who occupy or previously occupied the same geographic region or frequented similar locations as indicated by the user, and who have performed outdoor activities similar to those indicated by the user. The system can then: predict types of outdoor locations that the user may occupy and time periods in which the user may occupy these outdoor locations based on timestamped geolocation data collected from users in this cohort over previous supply intervals; and predict an unprotected ultraviolet exposure of the user during the upcoming supply interval based on historical ultraviolet irradiance data, such as based on actual ultraviolet indices detected by ultraviolet radiation sensor modules, associated with the cohort of users, when occupying such locations.

In a similar implementation, the system: identifies a cohort of other users—on the platform—characterized by demographics and preferred outdoor activities similar to those of the user, as described above; accesses ultraviolet exposure data of users in this cohort—such as derived from ultraviolet irradiance data collected by ultraviolet sensors integrated into mobile computing devices or standalone ultraviolet sensor modules associated with these users—during preceding supply intervals (e.g., one-year prior to the user's upcoming supply interval); and predicts the user's unprotected ultraviolet exposure—such as on daily time intervals—during the upcoming supply interval based on ultraviolet exposure data of other users in this cohort.

For example, for a representative user in this cohort, the system can: access a time series of local ultraviolet irradiance data measured by a ultraviolet sensor module—associated with the representative user—throughout a period of time preceding the user's upcoming supply interval; and integrate this time series of local ultraviolet irradiance values over the duration of this preceding period of time to estimate an unprotected ultraviolet exposure of the user during the upcoming supply interval or period of time therein. Alternatively, the system can: access a time series of locations occupied by the representative user on a particular day, such as from the representative user's smartphone; access a time series of ultraviolet irradiances at locations occupied by the representative user on this particular day, such as from a weather database; apply a predictive mathematical atmospheric ultraviolet radiation model (e.g., to account for current weather conditions); integrate these ultraviolet irradiances over corresponding periods of time in which the representative user occupied an outdoor space to calculate the representative user's cumulative unprotected ultraviolet exposure on this particular day; and repeat this process for other days for which location data for this representative user is available. Furthermore, the system can repeat this process for other representative users in the cohort to calculate unprotected ultraviolet exposures of these representative users during previous time periods that may be representative of the user's upcoming supply interval. The system can then: calculate an average (or maximum) unprotected ultraviolet exposure for representative users in this cohort, such as on one day; modify these values based on an atmospheric ultraviolet radiation model; add a safety factor (e.g., 20%) to this value; store the result as a predicted unprotected ultraviolet exposure for the user during a corresponding day in the upcoming supply interval; and repeat this process to predict unprotected ultraviolet exposures for the user on other days within the upcoming supply interval.

However, the system can implement any other method or technique to predict the user's unprotected ultraviolet exposure during a period (e.g., one hour, one day) of the user's upcoming supply interval.

(As described above, the system can similarly leverage a mathematical atmospheric ultraviolet radiation model constructed based on fundamental physics and geometries to predict the user's unprotected ultraviolet exposure during the upcoming supply interval.)

6. User Ultraviolet Exposure Limit

The system can then calculate an actual ultraviolet exposure limit for the user—such as maximum hourly, daily, weekly, and monthly ultraviolet exposures—based on the user's skin type and sun-related goals, sunscreen-related habits, history of prior sun exposure, etc., as shown in FIGS. 1 and 2.

In one implementation, the system implements a ultraviolet exposure model (e.g., a parametric or non-parametric model) that ingests skin type, sun-related goals, sunscreen-related habits, etc. and that outputs maximum hourly, daily, weekly, and monthly ultraviolet exposures. For example, paler skin types (e.g., light constitutional skin color and redder hair) may be correlated with greater likelihood of sunburn in the short-term and skin cancer in the longer term; accordingly, the model can output lower maximum allowable ultraviolet exposures per hour for users with paler skin (e.g., a lower skin type value), and vice versa. In another example, the model can output lower maximum daily and monthly ultraviolet exposures for users who selected or indicated a priority for reducing long-term skin cancer risk. Similarly, the model can output lower maximum hourly and daily ultraviolet exposures for users who selected or indicated a priority for preventing sunburns. The model can also output greater maximum hourly, daily, weekly, and monthly ultraviolet exposures for users who selected or indicated a priority for increasing tan.

Furthermore, the model can output greater maximum weekly and monthly ultraviolet exposures and/or specific exposure regimens for users who selected or indicated a priority for maintaining sufficient vitamin-D levels. In this example, the system can also output minimum weekly and monthly ultraviolet exposures predicted to maintain vitamin-D levels above a minimum threshold for these users.

Therefore, the system can programmatically: set a maximum allowable ultraviolet exposure for the user for an hour, day, week, or entire duration of the upcoming supply interval based on the user's skin type; increase the maximum allowable ultraviolet exposure if the user has exhibited a preference for increasing her tan or maintaining sufficient vitamin-D levels; and decrease the maximum allowable ultraviolet exposure if the user has prioritized preventing sunburns and reducing long-term risk of skin cancer; etc. However, the system can implement any other method or technique to set a maximum allowable ultraviolet exposure (and a minimum ultraviolet exposure) for the user for the user's first supply interval based on data collected from the user when initiating the user's profile.

In one example in which the user sets a goal of balanced healthy sun exposure, the system implements an ultraviolet exposure model (e.g., a parametric or non-parametric model) that ingests skin type, sun-related goals, sunscreen-related habits, etc. and that outputs maximum hourly, daily, weekly, and monthly ultraviolet exposures in the form of a progressive exposure regimen that prompts the user to gradually increase her sun exposure during the Spring in order to enable the user to produce sufficient vitamin-D while enabling the user's skin to adjust gradually to increasing sun exposure. The system can then select or define sunscreen formulas over this period of time according to this progressive exposure regimen.

7. Target Sunscreen Characteristics

Block S150 of the method S100 recites selecting a first sunscreen formula based on the first predicted unprotected ultraviolet exposure and the skin type of the user. Generally, in Block S150, the system can select a sunscreen formula from a population of existing sunscreen formulas or define a "custom" sunscreen formula (or specification for a "custom" sunscreen formula) for the user based on: predicted unprotected ultraviolet exposures over certain time intervals and/or at various locations during the upcoming supply interval and ultraviolet exposure limits calculated for the user for corresponding intervals (e.g., hourly, daily, and/or weekly ultraviolet exposure minimums and maximums); the user's skin type; skin sensitivities; the user's sunscreen-related habits; location-related limitations; the user's sun-related goals; sun protection product preferences (e.g., fragrance, all natural ingredients, moisturizers, on-skin appearance; skin-feel during application; product pigment or color; etc.); and/or types of outdoor activities that the user is predicted to perform or plans to perform during the upcoming supply interval.

7.1 Minimum UVA and UVB Protection Factors

In one implementation shown in FIGS. 1 and 2, the system: calculates minimum UVA and/or UVB sun protection factors that are predicted to reduce the unprotected ultraviolet exposure of the user—predicted for the upcoming supply interval—to less than the maximum allowable ultraviolet exposure specified for the user during the upcoming supply interval (e.g., during one hour, one day, or one week of the upcoming supply interval).

In one example, the system: calculates a maximum allowable ultraviolet exposure per day for the user based on the user's skin type, sun-related goals, sunscreen-related habits, etc., as described above; and identifies a maximum predicted unprotected ultraviolet exposure for the user per day within the upcoming supply interval based on predicted user locations, historical ultraviolet irradiance data at these locations, mathematical atmospheric ultraviolet radiation models, skin coverage by the user's attire (e.g., based on predicted user activities) at these locations, and predicted times that the user will occupy these locations during the upcoming supply interval. The system can then calculate minimum sun protection factors for a sunscreen that—if worn by the user—will reduce the maximum predicted unprotected ultraviolet exposure of the user on any single day of the upcoming supply interval to less than the maximum allowable ultraviolet exposure.

Additionally or alternatively, the system can calculate: a maximum allowable ultraviolet exposure per hour, per week, or per interval of any other duration for the user, such as described above; and then calculate minimum sun protection factors for a sunscreen that—if worn by the user—will reduce this maximum predicted unprotected ultraviolet exposure of the user during such intervals within the upcoming supply interval to less than the maximum allowable ultraviolet exposure. For example, the system can execute this process for multiple time intervals throughout the upcoming supply interval to calculate multiple minimum UVA and/or UVB sun protection factor values and then select or define a sunscreen formula or specification characterized by sun protection factors that exceeds all of these minimum sun protection factor values.

In a similar implementation, the system can execute methods described above to select or define multiple sunscreen formulas or specifications matched to sunscreen use regimens to meet the user's indicated goals. For example, a user who spends limited time outdoors, with the exception of weekends when her children have league soccer games, may set a goal of minimizing sun related skin aging. The system, taking into account the user's profile, skin type, activities, goals, preferences, locations, dates and times of predicted future exposure, etc., can specify a first sunscreen characterized by a UVB sun protection factor of "15" and characterized by a UVA sun protection factor of "10" contained in a broad-spectrum anti-aging moisturizing skin lotion for daily use. In this example, the system can also specify a second sunscreen characterized by a UVB sun protection factor of "50" and characterized by UVA sun protection factor of "30" contained in a broad-spectrum sunscreen for use during her children's soccer games on weekends.

7.2 Sun Protection Factor Adjustment

In the foregoing implementations, the system can also account for "half-life" of sunscreens or a particular sunscreen formula—that is, a reduction in the effectiveness of a sunscreen in reflecting or absorbing ultraviolet radiation over time, such as due to photo-degradation of active ingredients, effects of water and sweat, or removal from skin by clothing or towels during normal activities—when calculating the minimum UVA and/or UVB sun protection factors for a sunscreen formula for the upcoming supply interval. For example, the system can: implement the foregoing methods and techniques to calculate a minimum sun protection factors for a period of time within the upcoming supply interval; implement a sunscreen model (e.g., a parametric function or time-dependent equation) to predict the effective sun protection factors of sunscreen as a function of time following application of the sunscreen during this period of time; combine predicted unprotected ultraviolet exposure over this period of time with the effective sun protection factors—as a function of time—of a sunscreen characterized by this minimum sun protection factors in order to estimate actual ultraviolet exposure of the user during this period of time following application of sunscreen; and then increase the minimum sun protection factors if the estimated actual ultraviolet exposure of the user exceeds the maximum permitted ultraviolet exposure for this period of time.

The system can additionally or alternatively adjust the estimated actual ultraviolet exposure of the user to account for the user's sunscreen habits. For example, if the user exhibits a habit of delaying application of sunscreen until after some time (e.g., 20 minutes) of ultraviolet exposure, the system can increase the minimum sun protection factors in order to balance a period of direct, unprotected ultraviolet exposure prior to sunscreen application with higher ultraviolet protection after sunscreen application. Similarly, if the user exhibits a habit of delaying reapplication of sunscreen (e.g., if the users typically reapplies sunscreen on three-hour intervals rather than on two-hour intervals) or exhibits a habit of failing to reapply sunscreen altogether, the system can increase the minimum sun protection factors for the upcoming supply interval to compensate for the user's specific sunscreen application behavior. Additionally, if the user does not apply sufficient sunscreen to achieve the label characteristic UVA or UVB sunscreen protection factor of the sunscreen (e.g., as determined by a sensor-enabled sunscreen dispenser, from past user sunscreen use history, or from user self-reporting), the system can increase the minimum UVA and UVB sun protection factors for the upcoming supply interval to compensate for the user's specific sunscreen application behavior.

Furthermore, the system can adjust the sun protection factors to compensate for planned or predicted activities of the user during the upcoming supply interval. For example, for a period of time within the upcoming supply interval in which the user is predicted to perform an activity that reduces an effectiveness, half-life, or amount of sunscreen on the user's skin—such as swimming or performing strenuous activity that may cause the user to sweat, which may wash sunscreen from the user's skin, or which may rub the sunscreen off of the skin—the system can predict a reduction in the effectiveness of applied sunscreen and increase the minimum sun protection factors for the upcoming supply interval accordingly, such as described above. For example, the system can implement an activity model that predicts reduction in effectiveness of sunscreen as a function of both time and activity.

However, the system can implement any other method or technique to adjust the minimum UVA and UVB sun protection factors for the upcoming supply interval to compensate for user, location, activity, and/or sunscreen characteristics.

7.3 Other Characteristics

As described above, the user may indicate her sunscreen-related preferences (e.g., natural ingredients), medical conditions and skin sensitivities. The system can also retrieve sunscreen-related requirements for predicted locations of the user during the upcoming supply interval, such as: requirements for coral-safe sunscreens at a beach frequented by the user; or requirements for pool-safe sunscreens at a pool or athletic club frequented by the user. Similarly, the system can leverage a list of predicted activities of the user during the upcoming supply interval to specify or prioritize certain sunscreen characteristics, such as sweat-resistant sunscreens if the user is predicted to engage in frequent outdoor exercise during the upcoming supply interval. The system can specify characteristics of a sunscreen formula for the upcoming supply interval accordingly.

However, the system can specify any other limitations or priorities for a sunscreen formula for the upcoming supply interval based on data collected from the user during initialization of the user's profile.

7.4 Sunscreen Selection

The system can then select a particular sunscreen—from a set of existing sunscreens of known characteristics—for the user for the upcoming supply interval. In particular, the system can select a sunscreen formula characterized by a sun protection factors greater than the minimum sun protection factors calculated for the user for the upcoming supply interval and that fulfills other sunscreen-related limitations or priorities set by the system.

In one implementation shown in FIG. 2, after aggregating a minimum UVA and UVB sun protection factor, sunscreen-related limitations, and sunscreen characteristic priorities, as described above, the system can: access a database of existing sunscreen formulas; isolate (or "filter") a first subset of sunscreen formulas, in this database of existing sunscreen formulas, excluding components known to irritate a skin sensitivity indicated by the user (e.g., chemical barriers for sensitive skin); isolate a second subset of sunscreen formulas, in the first subset of sunscreen formulas, characterized by sun protection factors greater than the (adjusted) minimum sun protection factors for the upcoming supply interval; isolate a third subset of sunscreen formulas, in the second subset of sunscreen formulas, tailored for activities that the user is predicted to perform during the upcoming supply interval; and isolate a fourth subset of sunscreen formulas, in the third subset of sunscreen formulas, that fulfill or approximate the user's sunscreen-related preferences; and then select a particular sunscreen formula from the fourth subset of sunscreen formulas. For example, after isolating a set of sunscreens that fulfill minimum sun protection factors and skin sensitivity requirements, the system can: select a pool-safe sunscreen formula if the user is predicted to swim in an outdoor pool during the upcoming supply interval; select a sweat-resistant sunscreen formula if the user is predicted to engage in regular outdoor sports during the upcoming supply interval; and select an eco-friendly sunscreen formula if the user is predicted to visit a beach during the upcoming supply interval.

However, the system can implement any other method or technique to select an existing sunscreen that fulfills various requirements, limitations, and priorities for the user's upcoming supply interval. The system can then generate an order for a supply volume of the sunscreen to be mixed according to these proportions of sunscreen components.

7.5 Sunscreen Formula and Specification Calculation

Alternatively, the system can define a "custom" sunscreen formula by calculating proportions of various sunscreen components in order to meet the minimum sun protection factor, user preferences, sunscreen-related limitations, and sunscreen-related priorities for the upcoming supply interval, as shown in FIG. 1.

For example, the system can manage a set of sunscreen components, including: organic chemical ultraviolet barriers (e.g., oxybenzone, avobenzone, octisalate, octocrylene, homosalate, and octinoxate); mineral barriers (e.g., zinc oxide and titanium dioxide in nanoparticle and microparticle formats); carrier (e.g., oil, such as almond oil, coconut oil, Shea butter; moisturizing lotion); and additives (e.g., wax or oil to increase water and sweat resistance; antioxidants like tocopherol or diisobutyl adipate; colloids or solvents to adjust viscosity; emollients; stabilizing and photostabilizing agents; chelating agents; preservatives; humicants; emulsifiers; solvents; deoiling agents; skin feel modification agents; tints and colors; film-forming agents; and fragrances). The system can then implement a sunscreen model to calculate proportions of these components. For example, to achieve high UVA and UVB sun protection factor ratings, the sunscreen model can specify high proportions of chemical barriers (e.g., up to 15%) and mineral barriers (e.g., up to 50%) and a low proportion of carrier (e.g., less than 20%); because the resulting sunscreen may exhibit high viscosity, the sunscreen model can also specify a high proportion of solvent (e.g., butyloctyl salicylate) in order to reduce viscosity. In this example, if the user is predicted to engage in watersport or strenuous activity during the upcoming supply interval, the model can also increase a proportion of wax (e.g., beeswax or dimethicone) and solvent and reduce a proportion of carrier in the sunscreen formula accordingly. In another example, if the user has indicated a preference for maintaining or increasing her tan, has sensitive skin, and requires a lower minimum sun protection factor, the sunscreen model can specify a high proportion of Shea butter as a carrier, a lower proportion of mineral barrier (e.g., titanium dioxide microparticles), and no chemical barriers.

In a similar implement, the system can define a "custom" sunscreen specification by calculating properties of the sunscreen required to meet the minimum UVA and/or UVB sun protection factors, sunscreen-related limitations, user preferences, and sunscreen-related priorities for the upcoming supply interval, as shown in FIG. 1. For example, the system can manage a set of properties of the sunscreen such as: the UVA sun protection factor; the UVB sun protection factor; the level of water resistance (i.e. 40 minutes, 80 minutes, etc.); the level of sweat resistance; the types of active ingredients (reef-safe, all natural, non-nano, etc.); whether the sunscreen is moisturizing or not; whether the sunscreen is anti-aging or not; the on-skin appearance (e.g., the whitening effect of mineral ingredients); the intended use location on the body (face, arms, full body, etc.); the color or pigmentation; the fragrance; the form of the sunscreen (e.g., spray, rub-on stick, lotion, cream, paste, gel, liquid, etc.); whether the sunscreen is designed for hairy skin surfaces or not; whether the sunscreen is able to be applied to wet skin or not; whether the sunscreen exhibits anti-sand properties or not; the use scenario (daily use, activity specific use, etc.), etc.). The system can then implement a sunscreen model to calculate a specification of the sunscreen to meet the user's needs. For example, to achieve an anti-aging, daily moisturizing sunscreen for a fair-skinned resident of the southwestern United States, the sunscreen model can specify a product specification that includes: UVB sun protection factor "30"; UVA sun protection factor "20"; antioxidants; moisturizers; organic and mineral active ingredients; light, non-greasy lotion for application to the face and arms; light fragrance; no specific product color or tint; and no specific water resistance.

However, the system can implement any other method or technique to define a "custom" sunscreen formula or specification for the user for the upcoming supply interval.

7.6 Supply Interval

The system can implement the foregoing methods and techniques to predict the user's unprotected ultraviolet exposure during an upcoming supply interval or during periods (e.g., discrete hours, discrete days, or discrete weeks) within this upcoming supply interval and then leverage these predicted ultraviolet exposures to select a sunscreen formula or specification for the user and supply a volume of this sunscreen formula that is sufficient for the upcoming supply interval. In one implementation, the system implements fixed one-month supply intervals and thus implements the foregoing methods and techniques to: predict the user's unprotected ultraviolet exposure throughout the span of an upcoming one-month supply interval; select or define a sunscreen formula predicted to fulfill the user's sunscreen-related needs for this upcoming one-month supply interval based on unprotected ultraviolet exposure of the user for this period of time; and then supply a one-month supply of this sunscreen formula to the user accordingly.

For example, the system can calculate a volume of the sunscreen formula to cover the user's needs for the month based on: a cumulative unprotected ultraviolet exposure of the user during the upcoming supply interval; the skin area of the user (e.g., based on the user's height and weight), since greater skin area may necessitate more sunscreen in order to achieve desired sun protection; predicted peak ultraviolet intensities that the user will be exposed to during the upcoming supply interval (e.g., based on historical average or peak ultraviolet indices at times within the upcoming supply interval), since greater peak ultraviolet intensities may necessitate earlier initial application of sunscreen and more-frequent application of sunscreen thereafter; predicted or planned activities of the user during the upcoming supply interval, since water activities and higher-intensity activities (e.g., running, cycling) may require more-frequent application of sunscreen; predicted or planned use preferences (e.g., since a daily-use sunscreen for the face and arms may require greater volume than a weekend-only, face-only sunscreen over a period of time, such as one month); and/or the user's sunscreen-related habits, since a user who waits longer to first apply sunscreen after moving to an outdoor location may consume less sunscreen over time. Therefore, the system can estimate a volume of the sunscreen formula that may fulfill the user's needs during the upcoming supply interval based on the user's predicted unprotected ultraviolet exposure during the upcoming supply interval, predicted or planned activities of the user during the upcoming supply interval, the user's sunscreen-related habits, and/or other historical data or data collected from the user during initial setup of the user's profile. Additionally, if the user expects to travel by commercial airline, the container volume may be adjusted to allow carry-on compliance. For example, if a user travels frequently and uses a daily moisturizing sunscreen, she may require 6 ounces over a one month period, and the system can specify two 3-ounce tubes of sunscreen instead of one 6-ounce tube.

Alternatively, the system can predict the user's consumption of sunscreen during the upcoming supply interval—of fixed duration (e.g., one month)—based on historical sunscreen consumption by other users in the same cohort (as described above) on the platform.

Yet alternatively, the system can supply fixed volumes of the sunscreen formulas to users on the platform (e.g., four-ounce bottles) for supply intervals of variable length. In this variation, the system can implement methods and techniques similar to those described above to predict a duration of the upcoming supply interval for which this fixed volume of sunscreen will fulfill the user's sunscreens need.

Alternatively, the system can implement a fixed supply interval (e.g., one month) and a fixed supply volume (e.g., four ounces) and supply sunscreen to the user accordingly in preparation for the upcoming supply interval.

7.7 Sunscreen Supply

The system can then generate an order for a volume (e.g., one-month's supply) of the existing sunscreen selected or the customer sunscreen defined for the user's upcoming supply interval to be packaged and shipped to the user (e.g., to the user's home address) prior to the upcoming supply interval.

In one variation, the system also generates an order for a standalone ultraviolet sensor module to be shipped to the user with this first volume of sunscreen formula selected for the first upcoming supply interval following creating of the user's profile on the platform. Upon receipt of the ultraviolet sensor module, the user may attach the ultraviolet sensor module to her smartphone, to her bag (e.g., a purse, a backpack), to an article of clothing, or to a bottle or other container including the volume of sunscreen.

7.7 Multiple Sunscreen Formulas

In one variation in which the system determines that the user's sunscreen needs may differ substantively throughout the upcoming supply interval, the system can implement the foregoing methods and techniques to select or generate one sunscreen formula for each discrete or differentiable sunscreen need of the user. For example, if the user indicates that she spends weekdays typically indoors in a marine city characterized by high levels of daytime fog and that she spends most weekends outdoors gardening in a different, sunnier city, the system can: select or generate a first sunscreen characterized by low UVA and UVB sun protection factors for use during weekdays; and select or generate a second sunscreen characterized by a low UVA sun protection factor (e.g., to reduce skin damage and long-term skin cancer risk) and moderate UVB sun protection factor (e.g., to enable the user to achieve sufficient vitamin-D levels for an entire week given weekend exposure only) for use during weekends. The system can then supply both of these sunscreen formulas to the user for use during the upcoming supply interval.

8. Sunscreen Application Guidance

Furthermore, once the system has supplied the user with a sunscreen formula for the current supply interval, the system can selectively prompt the user to apply this sunscreen throughout the current supply interval, as shown in FIG. 2.

8.1 UV Exposure Tracking

In one variation, once the user creates her user profile and/or receives the first volume of sunscreen formula for her first supply interval, the system can interface with a mobile computing device carried by the user, a wearable device (e.g., a smartwatch) worn by the user, and/or a ultraviolet sensor module issued to the user (e.g., worn or carried by the user) to track the user's location, the user's activity, and ultraviolet indices proximal the user over time.

In one example, throughout the first future supply interval, the ultraviolet sensor module issued to the user can connect to and access its location from the user's mobile computing device and track its orientation. During a first sampling interval, in response to the orientation of the user's mobile computing device approximately aligning with a target direct orientation facing the Sun at a first time, the ultraviolet sensor module can record a first ultraviolet value read from the ultraviolet radiation sensor at approximately the first time as a direct ultraviolet value. Similarly, in response to the orientation of the user's mobile computing device approximately falling within a target diffuse orientation window biased away from the Sun at a second time, ultraviolet sensor module can record a second ultraviolet value read from the ultraviolet radiation sensor at approximately the second time as a diffuse ultraviolet value. Furthermore, in response to the orientation of the user's mobile computing device approximately aligning with a target global orientation facing vertically upward at a third time, the ultraviolet sensor module can record a third ultraviolet value read from the ultraviolet radiation sensor at approximately the third time as a global ultraviolet value. During the first sampling interval, the ultraviolet sensor module can calculate a first ultraviolet irradiance proximal the user's mobile computing device at its current location during the first sampling interval based on a combination of the direct ultraviolet value, the diffuse ultraviolet value, and the global ultraviolet value, such as described in U.S. patent application Ser. No. 15/648,158. The ultraviolet sensor module can: repeat this process during a second, subsequent sampling interval in order to calculate a second ultraviolet irradiance proximal the user's mobile computing device at its location during a second sampling interval; calculate an integral between the first ultraviolet irradiance and the second ultraviolet irradiance from the first sampling interval to the second sampling interval; and incorporate this integral into an actual unprotected ultraviolet exposure of the user between these sampling intervals. The ultraviolet sensor module can repeat this process over time throughout the current supply interval in order to track the user's actual unprotected ultraviolet exposure during a current hour, day, week, or other interval.

In another example, on a current day within the current supply interval, the user's mobile computing device, wearable device, or ultraviolet sensor module can: access a current location of the user's mobile computing device; based on the current location, a current time, and a current date, calculate a target direct orientation of the user's mobile computing device for which a primary axis of the ultraviolet radiation sensor is approximately normal to the Sun; track an orientation of the user's mobile computing device; in response to the orientation of the user's mobile computing device approximately aligning with the target direct orientation at the current time, storing a current value read from the ultraviolet radiation sensor at approximately the current time as a current direct ultraviolet value; and calculating a current ultraviolet irradiance proximal a current location of the user's mobile computing device at the current time based on the current direct ultraviolet value; and track a cumulative unprotected ultraviolet exposure of the user on the current day based on the current ultraviolet irradiance and preceding ultraviolet irradiances calculated at the user's mobile computing device on the current day;

Alternatively, the system can collect ultraviolet intensity data from a ultraviolet sensor integrated into the user's mobile computing device or wearable device and implement similar methods and techniques to calculate and track the user's actual unprotected ultraviolet exposure during the current supply interval.

Yet alternatively, the system can track the user's geospatial location via the user's mobile computing device or wearable device and then leverage ultraviolet irradiance data recorded by a local weather station to estimate the user's actual unprotected ultraviolet exposure during the current supply interval.

However, the system can implement any other method or technique to record and track actual user location and/or ultraviolet exposure data during the current supply interval once the system has supplied the user with a first sunscreen formula matched to this current supply interval.

8.2 Exposure-Based Sunscreen Application Prompts

In one implementation shown in FIG. 2, the system monitors the user's cumulative ultraviolet exposure—such as on the current day and/or on the current week (e.g., seven-day period)—through the user's mobile computing device, wearable device or standalone ultraviolet sensor module carried by user, as described above. When the system can determined that the user's cumulative ultraviolet exposure for the current day reaches a threshold proportion (e.g., 30%) of a maximum permitted ultraviolet exposure for the user, the system can serve a prompt to the user to apply sunscreen supplied for the current supply interval, such as in the form of: a SMS text message; an in-application notification at the user's mobile computing device or wearable device; or an audible or visual alert at the user's ultraviolet sensor module. Additionally or alternatively, the system can serve a prompt to the user to apply sunscreen supplied for the current supply interval when the user's cumulative ultraviolet exposure for a current, contiguous period of ultraviolet exposure reaches a threshold proportion (e.g., 15%) of a maximum permitted ultraviolet exposure for the user for one hour, for one day, or for another tie interval.

However, the system can serve a prompt to the user to apply the supplied sunscreen formula for the current supply interval in any other way in response to a cumulative unprotected ultraviolet exposure of the user exceeding a threshold unprotected ultraviolet exposure or in response to any other ultraviolet-exposure-related event.

8.3 Location-Based Sunscreen Application Prompts

In another implementation, the system can define geofenced areas in which humans often spend extended periods of time in direct or diffuse sunlight and assign triggers for sunscreen application to these geofenced areas, such as: beaches; rivers; lakes; ski resorts; remote areas with low density of buildings (e.g., wildlife preserves, national parks, state parks, city parks, etc.); fields (e.g., soccer fields, football fields, baseball fields, tennis courts); open-air stadiums (e.g., baseball, football stadiums); parking lots; and/or parks; etc. The system can then monitor the user's location over time through the user's mobile computing device and then prompt the user—such as via a SMS text message or in-application notification on the mobile computing device—to apply sunscreen when the user enters a geofenced area during a period of time in which the Sun is overhead at this geofenced area or in which a measured or predicted ultraviolet irradiance exceeds a threshold ultraviolet irradiance.

For example, the system can prompt the user to apply sunscreen supplied for the current supply interval if the user has entered and remained within a geofenced area tagged with a sunscreen application trigger for more than a threshold duration of time, such as a fixed duration of time (e.g., five minutes) or a duration of time inversely proportional to a measured or estimated ultraviolet irradiance within this geofenced area.

However, this system can serve a prompt to the user to apply sunscreen supplied for the current supply interval responsive to any other location-based trigger.

Conversely, if the system determines that the user has experienced less than a minimum cumulative ultraviolet exposure during a current time period (e.g., the current day, the current seven-day period), such as according to methods and techniques described above, the system can instead prompt the user to delay or avoid application of sunscreen in order to increase cumulative ultraviolet exposure and thus increase the user's vitamin-D. Subsequently, once the user's cumulative ultraviolet exposure reaches or approaches a minimum ultraviolet exposure—corresponding to a minimum estimated vitamin-D level—for the current time period, the system can implement the foregoing methods and techniques to prompt the user to apply the supplied sunscreen.

8.4 Sunscreen Application Confirmation

In one variation shown in FIG. 2, the system further prompts (or enables) the user to manually confirm application of the supplied sunscreen, such as by swiping a notification at the user's mobile computing device or confirming application of the supplied sunscreen within the native application executing on the user's mobile computing device. Additionally or alternatively, the sunscreen for the current supply interval can be supplied in a bottle (or other container) that includes a sensor configured to detect dosing events (e.g., an accelerometer that detects inversion of the bottle, which may be interpreted as a dosing event, or a switch that detects the state of the lid, such as open or closed) and a wireless communication module configured to output dosing event data to the user's mobile computing device. In this implementation, the system can thus access a time series of dosing events or individual detected dosing events detected by this bottle in order to automatically track sunscreen application and consumption by the user throughout the current supply interval.

However, the system can implement any other methods or techniques to track sunscreen application and consumption by the user throughout the current supply interval. Furthermore, the system can derive the user's sunscreen related habit based on this sunscreen application and consumption, such as by deriving correlations between application of sunscreen and one or more of: time of day; location; local ultraviolet irradiance, such as calculated based on concurrent ultraviolet irradiance detected by the user's ultraviolet sensor module; and the user's sunscreen use history.

8.5 Sunscreen Reapplication Prompt

Furthermore, based on known characteristics of the sunscreen formula supplied to the user for the current supply interval, a detected or estimated ultraviolet irradiance or ultraviolet irradiance near the user, the actual cumulative ultraviolet exposure of the user during a current time interval, a current activity of the user (e.g., detected directly by the user's mobile computing device or wearable device based on motion; or predicted based on the user's location), and a time of a last confirmation of application of the supplied sunscreen by the user, the system can serve a prompt to the user to re-apply the supplied sunscreen, as shown in FIG. 2.

In one example, the system: accesses a model for predicting tendency of sunscreens to bind to skin as a function of component types and component proportions contained in sunscreens formulas; and inputs a formula of the supplied sunscreen into the model to predict a half-life of the supplied sunscreen. After the user confirms application of the supplied sunscreen, the system can initiate a timer for reapplication of the supplied sunscreen as a function of its half-life time. (The system can also adjust the duration of this timer based on the sunscreen label instructions or based on the user's current activity and local conditions, such as by: reducing the duration of the timer by 50% if the user is predicted to be swimming; reducing the duration of the timer by 30% if the user is predicted to be running or cycling; reducing the duration of the timer by for greater local ultraviolet indices; and increasing the duration of the timer if the user is predicted to be occupying a shaded area.) When this timer expires, the system can serve a prompt to the user to reapply the supplied sunscreen, such via SMS text message, in-application notification, or an alert at the ultraviolet sensor module such as described above.

The system can therefore prompt the user to reapply sunscreen based on both characteristics of the sunscreen and local conditions in order to limit probability that the user's actual cumulative ultraviolet exposure exceeds the maximum allowable ultraviolet exposure specified for the user during the current time period within the current supply interval.

Alternatively, the system can serve a prompt to the user to re-apply the supplied sunscreen on a regular interval, such as every two hours, while the user is thus determined to be outdoors or otherwise exposure to significant levels of ultraviolet radiation.

8.6 Sun Avoidance Prompt

Furthermore, the system can implement methods and techniques described above to track the user's cumulative unprotected ultraviolet exposure during the current period of time, such as the current hour, day, or week within the current supply interval. The system can then combine this cumulative unprotected ultraviolet exposure with known initial UVA and/or UVB sun protection factors of the supplied sunscreen, a predicted change in the sun protection factors of the supplied sunscreen as a function of time since application (and user activity, etc.), a time that the user applied (and reapplied) the sunscreen (e.g., based on manual confirmation from the user or dosing events detected automatically), and/or a predicted or user-indicated skin coverage by garments worn by the user to estimate the user's actual cumulative ultraviolet exposure during the current period of time. Then, in response to the actual cumulative ultraviolet exposure reaching a maximum allowable ultraviolet exposure (or falling within a threshold proportion of the maximum allowable ultraviolet exposure, such as 90% of the maximum allowable ultraviolet exposure) for the current period of time (e.g., the current hour or day), the system can serve a prompt to the user to find shade, move inside, or other avoid further sun exposure.

For example, on the current day, the system can: calculate a maximum allowable ultraviolet exposure per day for the user based on the user's skin type; receive confirmation from the user, via the user's mobile computing device, of application of the supplied sunscreen formula at a first time; track actual cumulative ultraviolet exposure of the user on the current day based on the cumulative unprotected ultraviolet exposure on the current day up to the first time and cumulative unprotected ultraviolet exposure on the current day after the first time adjusted based on an initial sun protection factors of the supplied sunscreen formula and a half-life of the supplied sunscreen formula; and then serve a prompt to the user to seek shelter from the Sun in response to the actual cumulative ultraviolet exposure of the user on the current day exceeding the maximum allowable ultraviolet exposure per day for the user.

However, the system can implement any other method or technique to prompt the user to avoid further sun exposure in any other way responsive to the actual cumulative ultraviolet exposure of the user during a current period of time exceeding a maximum allowable ultraviolet exposure for the user for this period of time.

8.7 User Survey

Throughout the current supply interval, the system can prompt the user to submit additional sun-exposure related feedback. For example, the system can prompt the user—such as via the user portal within the native application executing on the user's mobile computing device—to indicate: whether the user has experienced a sun burn and a degree of this sunburn; whether the user's tan has changed and a degree of this change; if the on-skin appearance of the sunscreen, once applied, is acceptable to the user; if the skin-feel of the sunscreen, once applied, is acceptable to the user; if the color or tint of the sunscreen, once applied, is acceptable to the user; if the fragrance of the sunscreen is acceptable to the user; and/or whether the user has experienced sensitivity or an allergy to the sunscreen formula supplied to the user for the current supply interval. For example, the system can query the user for sunburn-, tan-, and allergy-related feedback: two hours after a period of intense or above-average ultraviolet exposure; on a day after prolonged outdoor activity; on weekly intervals throughout the current supply interval; and just before re-executing the foregoing methods and techniques to select or define a second sunscreen formula for the next supply interval.

9. Next Sunscreen Formula

Therefore, the system can collect unprotected ultraviolet exposure data, location data, activity data, sunscreen application data, user preference data; sunburn- and tan-related feedback, and/or skin sensitivity feedback, etc. for the user during the current supply interval. The system can then implement the foregoing methods and techniques—now based (more predominantly) on these user-specific data—to select a different sunscreen formula or to adjust the sunscreen formula for the user for the next supply interval, as shown in FIG. 2.

9.1 Feedback-Based Sunscreen Formula or Specification Adjustment

In one example, if the user indicated that she experienced a sunburn despite application of sunscreen as directed by the system, the system can: increase the minimum sun protection factors designated for the next supply interval; adjust the user's predicted skin type to reflect a more sun-sensitive skin type; predict that the user's activities when outdoors (e.g., swimming, exercising) reduced effectiveness of the last supplied sunscreen and specify a higher water-resistance requirement for the sunscreen formula for the next supply interval; and/or update the user's profile to reflect more-frequent sunscreen application prompts for the user during the next supply interval. In this example, if the user indicated that she had significant leftover sunscreen at the conclusion of the current supply interval, the system can also predict that the user applied too little sunscreen during each dosing event and either: specify chemical and/or mineral barriers with greater effectiveness (e.g., ultraviolet rejection or absorption) per unit volume; and/or serve additional guidance to the user—such as via the native application—to inform the user about how much sunscreen to apply per dosing event.

In another example, if the user indicated that she experienced a rash or other sensitivity to the sunscreen formula supplied during the current supply interval, the system can specify or define a sunscreen formula with different active ingredients for the next supply interval.

In yet another example, if the user indicated that her tan diminished during the current supply interval despite a preference to maintain or increase her tan, the system can: decrease the minimum sun protection factors designated for the next supply interval; adjust the user's predicted skin type to reflect a less sun-sensitive skin type; and/or update the user's profile to reflect less-frequent sunscreen application prompts for the user during the next supply interval.

The system can then implement the foregoing methods and techniques to select an alternative sunscreen formula from a population of existing sunscreen formulas or define an alternative sunscreen formula for the next supply interval according to these revised parameters thus generated by the system based on user feedback and other data collected during the current supply interval.

9.2 Next Sunscreen Formula

In another implementation, the system records: a time series of actual ultraviolet irradiance values proximal the user—such as detected by the user's ultraviolet sensor module or mobile computing device—during the current supply interval (or period therein); tracks the user's location throughout the current supply interval; and integrates this time series of actual ultraviolet irradiance values over the duration of the current future supply interval to calculate an actual cumulative unprotected ultraviolet exposure of the user during the current supply interval (or period therein). The system then: predicts locations that the user will occupy during the next supply interval (e.g., based on locations occupied by the user during the current supply interval, activities of other similar users, and/or the user's calendar, etc., as described above); and calculates a predicted unprotected ultraviolet exposure of the user during this next supply interval based on historical ultraviolet irradiance data for these predicted locations. If the actual cumulative unprotected ultraviolet exposure of the user exceeded the predicted unprotected ultraviolet exposure of the user during the current supply interval, the system can increase the predicted unprotected ultraviolet exposure for the user for the next supply interval; and vice versa. The system can then: calculate a new minimum sun protection factors predicted to reduce the predicted unprotected ultraviolet exposure for the next supply interval to less than the maximum allowable ultraviolet exposure specified for the user; select a second sunscreen formula—different from the sunscreen formula previously supplied to the user—characterized by sun protection factors greater than the new minimum sun protection factors; and then supply a volume of this second sunscreen formula to the user.

Therefore, the system can collect user-specific data regarding where the user spends her time, her activities, and her ultraviolet exposure, etc. during a current supply interval and then leverage these data to select or define a sunscreen formula for the user's next supply interval. The system can repeat this process for each subsequent supply interval over time, thereby adjusting sunscreen formulas supplied to the user to compensate for environmental (e.g., seasonal) changes, changes in the user's preferences and outdoor activities, changes in the user's skin sensitivities, and/or changes in user's location, etc. over time.

9.3 Location Change

In another implementation, the system can: access the user's current geospatial (e.g., GPS) location; and compare this location to the user's previous geospatial location (e.g., a primary geospatial location established in the user's profile during the setup process) to determine whether the user is now occupying a location significantly different from (e.g., of 50 miles of) the user's previous geospatial location, such as for a significant period of time (e.g., more than one day). If so, the system can then: assess whether this new location constitutes a new ultraviolet exposure condition for the user (e.g., an elevation change during a ski trip); then prompt the user to indicate new outdoor activities the she anticipates performing while in this new location; and select or calculate a new sunscreen formula for the user, such as if requested by the user.

10. Planned Special Events

In one variation in which the user has planned a unique outdoor activity characterized by potential sun exposure that differs significantly from potential sun exposure of the user's common outdoor activities during the current and/or past supply intervals, the system can interface with the user to aggregate relevant data and to select or define a different sunscreen formula specific to this unique outdoor activity. For example, if the user lives in a location characterized by frequent overcast skies and rain during an upcoming supply interval but the user is planning a one-week trip to a sunny beach resort, the system can implement methods and techniques described above: to select or define a first sunscreen formula for use in the user's home location; to select or define a second sunscreen formula for use at the beach resort (e.g., based on ultraviolet exposures typical of other users on the platform who have visited this beach resort and/or based on historical ultraviolet irradiance data in the location of the beach resort for the time of year that the user has planned this one-week trip); and supply both the first and second sunscreen formulas to the user for the next supply interval.

Therefore, in the foregoing example, the user can manually request a second sunscreen formula specific to a unique location that the user intends to visit during the next supply interval. Alternatively, the system can: predict locations that the user will occupy during the next supply interval based on the user's calendar or other data supplied by the user; identify two (or more) locations characterized by significantly different ultraviolet indices during the next supply interval; determine that one sunscreen formula may be insufficient to meet the user's sun-related needs and goals at these two locations; and then automatically elect to supply the user with two unique sunscreen formulas (e.g., a low-sun protection factor sunscreen at the user's home location and a high-sun protection factor sunscreen for the beach resort) for the next supply interval.

In a similar example, during a current supply interval, the system can: receive confirmation from the user—such as via the native application—of a plan to visit a new location during a time period within the current supply interval, wherein this new location is excluded from locations that the user has visited regularly in the past or previously indicated that she would visit during the current supply interval; and receive a request for a new sunscreen formula accordingly. For example, if the user decides to take a skiing trip the following weekend, the user may indicate this ski trip, the duration of the ski trip, the location of the ski trip, and the user's intended activities during this ski trip within the native application executing on her mobile computing device. Based on historical ultraviolet irradiance data for new location indicated by the user and based on a duration of the time period that the user intends to occupy this new location, the system can calculate a new predicted unprotected ultraviolet exposure of the user during this time period. The system can then calculate a new minimum sun protection factors predicted to reduce the new predicted unprotected ultraviolet exposure to less than the maximum allowable ultraviolet exposure specified for the user, as described above. If the new minimum UVA and UVB sun protection factors exceeds the sun protection factors of the sunscreen formula already supplied to the user for the current supply interval, the system can: select a second sunscreen formula characterized by a second set of UVA and UVB sun protection factors greater than the new minimum UVA and UVB sun protection factors; and ship a second volume of the second sunscreen formula to the user prior to this period of time (e.g., prior to the user leaving for the ski trip). Alternatively, if a time to ship the second sunscreen formula to the user is greater than a time to the user's departure to this new location, the system can instead: identify a particular manufacturer and line of sunscreen that substantially matches these sunscreen parameters calculate for the new location; and then prompt the user to purchase this particular manufacturer and line of sunscreen locally.

The system can implement similar methods and techniques to guide the user in selecting and purchasing sunscreen from an external supplier, such as if the user lost her supplied sunscreen for the current supply interval or if the user arrived at a location of a planned outdoor activity during the current supply interval without her supplied sunscreen.

11. No Sunscreen Condition

In one variation, if a predicted unprotected ultraviolet exposure of the user for a next supply interval is less than a minimum ultraviolet exposure, the system can elect to defer supply of a sunscreen formula to the user for this next supply interval. For example, the system can calculate maximum unprotected daily and weekly ultraviolet exposures for which the user may not require sunscreen in order to minimize risk of sunburn; if the daily and weekly predicted unprotected ultraviolet exposures of the user for the next supply interval are less than these maximum unprotected daily and weekly ultraviolet exposures, the system can elect to not supply the user with sunscreen during this next supply interval.

Furthermore, the system can predict minimum daily and weekly ultraviolet exposures that will maintain the user's vitamin-D levels above a minimum level, such as based on the user's age and skin type. If these minimum daily and weekly ultraviolet exposures to maintain the user's vitamin-D level are less than the predicted unprotected daily and weekly ultraviolet exposures of the user during this next supply interval, the system can elect to supply the user with a vitamin-D supplement rather than sunscreen for this next supply interval.

12. System

As shown in FIGS. 3-7, a dispenser system 100 for tracking and communicating sunscreen use includes: a sunscreen container with a sunscreen dispensing means; a sensor arranged on the container; a wireless communication means configured to output information about said container and events detected by said sensor; a power supply to power the electronic elements of the system; and a software program. The sunscreen container is configured to dispense sunscreen with: a closure; an identification label; and a dispensing port. The sensor is configured and arranged on the sunscreen container to detect the state of the container closure. The software program is configured: to access stored information from the identification label about the sunscreen container; to access the state of the container closure based on the sensor state; to associate changes in the state of the container closure with date and time information; to record the container closure state and state change with the date and time information associated with the state change event, and to wirelessly communicate this information to a remote computing platform or device.

12.1 Applications

The dispenser system 100 includes a sunscreen container, a sensor, a software program running on a processor, and a sunscreen dispensing means that cooperate to form a "sunscreen dispenser" configured to track and report on sunscreen usage by one or more users. The sunscreen dispenser is configured to access information about the sunscreen (e.g., the sun protection factor, or "SPF", of the sunscreen, the sunscreen brand, or the sunscreen type, such as water-resistant, or zinc-oxide) contained from the identification label, to record sunscreen usage and to communicate this information to a another device to allow a user to accurately track his sunscreen usage over time. A software program, such as on a phone, activity tracker, mobile computing platform or other device, can receive this sunscreen usage information from the sunscreen dispenser and combine the information with real-time or forecast solar irradiance measurements (e.g., visible light, UVA, UVB, UVC, ultraviolet irradiance, and IR), the user's sunscreen application history, the user's personal sun exposure information (like skin type, age, height, weight, or past ultraviolet exposure history), as well as various other data to provide guidance, sun exposure tracking, alerts, alarms and reminders for safe sunscreen use and safe sun exposure practices. The information provided to the user may include, for example, but is not limited to: when to reapply sunscreen; an appropriate sunscreen type and sun protection factors for the current conditions; timers and reminders to reapply sunscreen; when the sunscreen container is empty; how much sunscreen has been applied; when to seek shelter from the sun; when to wear additional sun protective clothing; how much sun exposure the user has received; and how much vitamin D the user has synthesized as a result of sun exposure over a period of time.

Sunscreens are typically characterized by a two sun protection factors: SPF, which describes the effectiveness of the sunscreen in blocking or absorbing incoming UVB radiation (herein UVB sun protection factor); and PFA, which describes the effectiveness of the sunscreen in blocking or absorbing incoming UVA radiation (herein UVA sun protection factor). An SPF of 15, for example, lets $\frac{1}{15}^{th}$ of the incoming UVB radiation penetrate to the skin, allowing a person with SPF 15 sunscreen properly applied to her exposed skin to remain in the Sun for 15 times longer than she would without sunscreen and to receive the same overall UVR exposure. For example, if, under a specific set of environmental conditions, a person can remain exposed to the Sun without any sunscreen for 20 minutes before she risks a sunburn, then with SPF 15 sunscreen properly applied she can remain in the Sun for 30 minutes (SPF 15×20 minute base exposure with no sunscreen) before risking a sunburn.

Direct exposure of a person's skin to solar radiation has various effects on the individuals health, including both detrimental effects (e.g., sunburn, skin damage, increased risk of skin cancer, sun pigmentation spots, accelerated skin aging and immune system suppression) as well as beneficial effects (e.g., cutaneous vitamin D synthesis, cutaneous nitric oxide release, improved emotional state, and reduced symptoms of some diseases). While short-term or low-level exposures may have net positive effects on a person's overall health, depending on the environmental conditions and the person's specific needs and characteristics, prolonged sun exposure may have net negative effects. The use of sun protective measures (e.g., the application of sunscreen) can protect the skin from some amount of ultraviolet radiation for a period of time after application. The effectiveness of sunscreen and the duration of associated protection of the skin from UVR are dependent on a number of factors including the UVA and UVB sun protection factors of the sunscreen, the intensity of the UVR, the amount of sunscreen applied, exposure to water or sweat, the type of sunscreen, the re-application intervals, the UVR exposure levels, the type of sunscreen as well as other factors. Different types of sunscreens may vary in a number of ways including the UVA and UVB sun protection factors (sun protection factors), the presence or absence of UVR blocking ingredients (e.g., zinc oxide or titanium dioxide), the presence or absence of UVR absorbing ingredients (e.g., oxybenzone, avobenzone, octisalate, octocrylene, homosalate, octinoxate, and others), the UVR band protection (UVB protection vs. broad-band UVA and UVB protection), the resistance to water exposure, etc.

Because the effectiveness of sunscreen is dependent on many various factors, as described above, it may be important for a person exposed to UVR to understand how and be able to balance these various factors in order to minimize the sun exposure risks while maximizing the sun exposure benefits. While ultraviolet monitors (e.g., handheld electronic devices equipped with ultraviolet photo-sensors) can measure the levels of UVR that a person is exposed to and can track the individual's overall ultraviolet exposure, the actual exposure a person's skin experiences is dependent on the sunscreen she has applied, among other factors. Furthermore, even when applied properly, sunscreen will lose its effectiveness over time due to degradation of the ingredients, washing off with water or exposure to sweat, rubbing off from clothing or towels, etc., and will need to be reapplied to maintain the sun protection effects. For these reasons a person who is exposed to the Sun may track their level of exposure as well as their sunscreen usage and sun protection factors to properly balance safe sun exposure and minimize the detrimental effects of prolonged sun exposure.

UV monitors are commonly used in the fields of atmospheric physics, meteorology, biology, botany, and worker safety, among others. Various forms of ultraviolet monitors have made their way into consumer products to allow users to better monitor their ultraviolet exposure, especially ultraviolet exposure associated with solar irradiance when, for example, a person is outdoors exposed to the sun. ultraviolet monitors may take many forms including: stationary environmental monitoring devices; highly accurate portable radiometers; handheld and/or pocket-sized radiometers (often using ultraviolet sensitive photodiodes, phototransistors or other electronic ultraviolet sensors); color changing (non-electronic) products like wrist bands, adhesive patches, etc.; and software programs running on stationary or portable computing platforms (e.g., on a smartphone, smartwatch, activity monitor, tablet computer, laptop computer, desktop computer, computer server, website, or other computing device) that have access to ultraviolet irradiance (including ultraviolet irradiance) measurements, forecasts, models, or other ultraviolet-related information that may be of use to a user exposed to the sun. For the purposes of this invention the term "UV monitor" shall refer to any and all types, forms or embodiments of devices, software, services, etc. that provide, either directly or indirectly, one or more individuals with past (historical), present, and/or future (forecast) information related to environmental and/or solar UVR, ultraviolet irradiance, ultraviolet irradiance, and/or any other ultraviolet related measure relevant to an individual's ultraviolet exposure. As one example, a variation of a ultraviolet monitor may be in the form of a software application running on a smartphone, with access to ultraviolet irradiance forecasts provided by the National Weather Service or the Environmental Protection Agency, and which provides this forecast ultraviolet irradiance information to a user. A second example of a variation of a ultraviolet monitor is a handheld electronic device, shown in FIG. 3, configured to include a ultraviolet irradiance sensor and configured to read ultraviolet irradiance, convert the ultraviolet irradiance to erythemally active ultraviolet irradiance and ultraviolet irradiance (through the use of ultraviolet filters, algorithms, etc.), and offer a user with a ultraviolet irradiance measurement along with guidance related to how much exposure may result in skin damage, in sunburn (i.e. erythema), in a desired amount of cutaneous synthesized vitamin D production, etc.

The dispenser system 100 can therefore include: a sunscreen dispenser configured to access stored information on a sunscreen identification label and monitor the times and amounts of a specific sunscreen dispensed; and a software program configured to record and wirelessly communicate this information to a remote computing platform (e.g., a smartphone, computer, server, ultraviolet monitor, smartwatch, or other device) via cellular signal, local area communication (e.g., Bluetooth, etc.), WiFi network, etc., to a local mobile computing device or hub or other target. Based on this information the remote computing platform may update a person's sunscreen application tracking information including the sunscreen type, sun protection factors, the time and date of application or reapplication, and the amount of sunscreen applied to allow for accurate exposure tracking and reminders, alerts and alarm updates for safe and healthy sun exposure for the user. Alternatively, the sunscreen dispenser may store various usage-related data, such as the amount of sunscreen dispensed, the date and time that sunscreen has been dispensed, sunscreen specific information read from the sunscreen identification label, the amount of sunscreen remaining in the sunscreen dispenser, etc., and can return these data to the remote computing platform, server, smartphone, watch, server, or other device. However, elements of the dispenser system 100 can be of any other form and packaged in any other way to collect, process and communicate sunscreen usage data, either synchronously or asynchronously, from one or more usage events over time.

12.2 Container and Sensors

The dispenser system 100 includes a sunscreen container configured to house an amount of sunscreen for one or more applications by a user, including: an enclosure to house the sunscreen; a volume or amount of sunscreen within the container; and an identification label affixed to the container with information which may include, but is not limited to, the type of sunscreen, the sunscreen active ingredients, the UVA and UVB sun protection factors of the sunscreen, the brand of sunscreen, the recommended amount of sunscreen per application, the number of applications of sunscreen in the container, the volume of sunscreen in the container, the UPC code, specific use characteristics (e.g., water resistance, etc.), and/or any other product identification or product specific information. The identification label may be contain information that may be read by optical means (e.g., a barcode or QR code), magnetic means, electronic means (e.g., an RFID tag, a microchip, etc.), physical means (e.g., specific positional features that may represent information), or it may contain an identifier number or code that refers to a specific product and its associated information (as described above) in a database (e.g., a UPC code).

The sunscreen container may be pre-filled and/or re-Tillable and contain a volume of liquid sunscreen, a volume of cream or emulsion sunscreen, a volume of aerosol or otherwise sprayable sunscreen, a volume of solid rub-on sunscreen, one or more pre-packaged fixed volume sunscreen packets (e.g., single dose foil packs, or tubes, etc.), one or more tissue or fabric wipes imbued with sunscreen (suitable for rubbing on the skin in a fashion similar to a moist towlette). The container may take the form of a tube, a bottle, a jar, a box, a spray bottle, a pump bottle, a stick applicator (similar to a deodorant applicator), or any other suitable form to package and contain any form of sunscreen.

The sunscreen container may include one or more means to physically connect to or mount onto another object, a tether, a Velcro pad, a clip, a snap, a clamp, etc.

In one variation, elements of the system are integrated into a ultraviolet monitor, ski pole, a bicycle, a kayak or canoe, a beach umbrella or other beach shelter, a beach chair, a lawn chair, a cooler, a pool-side recliner chair (or any other type of seating), a water or hydration bottle, an athletic hydration pack or hydration belt, a hat, or other outdoor or sport-related or activity-related object; and the software program implements methods and techniques to record and track sunscreen use via sensors in the sunscreen dispenser connected to the object, and communicates this sunscreen use data to another device either through wired or wireless communication means.

In another variation, the sunscreen container includes one or more sensors configured to measure one or more of the following: the action of dispensing of sunscreen from the container; the actuation of a dispensing means (e.g., a pump or button actuation), the volume of sunscreen dispensed; the state of one or more elements of the container (e.g., the movement or position of a plunger); the volume of sunscreen within the container; an electronic signal (e.g., from an electrical button, or from electrical contacts); a wired or wireless communication signal; the connection to another physical object (e.g., a dispensing lid, a ski pole, a hydration belt, or any other object to which the container may be physically connected), the presence of an RFID tag or other identification means, etc.

12.3 Dispensing Means and Sensors

The dispenser system 100 also includes a means to dispense sunscreen from the container configured to allow a user of the sunscreen dispenser to dispense sunscreen when desired. For example, a cream or emulsion may be dispensed through an opening port in the container by squeezing the container; through a spray nozzle on a pressurized sunscreen container by pressing a dispensing button on the pressurized spray container releasing a spray or aerosol of sunscreen; through a spout on a bottle of sunscreen by moving a pump actuator to dispense a liquid, cream or emulsion sunscreen; through a door or other opening port in the container allowing a user to remove a sunscreen-imbued tissue, towlette, sponge, cloth or other soft and/or flexible applicator so that the user may wipe the sunscreen-imbued applicator on his skin to apply the sunscreen; or any other dispensing port and means of dispensing any form of sunscreen from any form of sunscreen container. The means of dispensing the sunscreen from the container may be through a user-powered activation, such as squeezing a tube or activating a dispensing trigger, for example, or dispensing may be through a powered actuator wherein the actuator provides the means and power to dispense the sunscreen from the container such as in a pressurized spray container, or spring loaded piston dispenser, or an electric motor powered lead screw dispenser, or any other powered or unpowered means of dispensing sunscreen from the container. In one embodiment a sunscreen dispenser configured to dispense a fixed or user-determined volume of sunscreen by actuation of an electric motor, which in turn is controlled by a motor controller circuit, which in turn is controlled by means of a processor receiving an electric signal from a button or remote device, for example.

The dispensing means is further equipped with one or more sensors that are configured to detect one or more of: the dispensing of sunscreen; the volume or amount of sunscreen dispensed; the amount of sunscreen remaining in the container; the actuation of a button, lever, switch, trigger, or other interface or input element; an electronic signal; and/or the identity of the user to whom the dispenser is dispensing sunscreen (e.g., through an RFID, magnetic signal, electric signal, fingerprint or other biometric signal, proximity to a person, proximity to an electronic device or a wrist-worn device or bracelet or tag, a hotel or resort room key, detection of a password or code entry, a wireless signal, or any other means allowing the system to identify and track which user has or is using the sunscreen dispenser).

The dispenser system 100 further includes a means to communicate with a computing platform by means of wired and/or wireless communication means. For example, the sunscreen dispenser may use a Bluetooth wireless communication protocol to communicate with a ultraviolet monitor device, so as to allow the ultraviolet monitor device to more accurately track a user's sunscreen use and provide guidance, alerts, alarms and advice for safe sun exposure practices. The sunscreen dispenser may communicate with more than one of: a portable computing platform; a portable electronic device; a computer; a phone; a wrist watch; an activity tracker; a bicycle computer; a bicycle equipped with a computer platform; a server; a database; another sunscreen dispenser; a Wi-Fi network; a router; a website; or any other proximal or remote device or network.

In one example, the sunscreen dispenser system 100 communicates to a computer by means of a USB wired communication cable to provide a synchronization of data and to recharge a power supply (e.g., a battery) on the sunscreen dispenser.

In another example of the dispenser system 100, the sunscreen dispenser communicates with one or more ultraviolet monitors and one or more other sunscreen dispensers to form a communication network, allowing a user to choose between more than one of the different sunscreens, contained in the various sunscreen dispensers. In this manner, a connected ultraviolet monitor may provide the user with guidance (based on the ultraviolet irradiance or ultraviolet irradiance) related to when it is advisable to switch to a sunscreen with different properties, such as an increased sun protection factors, or water resistance, etc.

In another example of the sunscreen dispenser system 100, the dispensing means is a dispensing cap for a sunscreen tube, including: a dispensing sensor to detect when sunscreen is dispensed; a means to read an identification label on a sunscreen dispenser to which the dispensing cap is attached; a wireless communication means; a rechargeable battery; a photovoltaic solar cell configured to recharge the battery; and a software program. In this example when the dispensing cap is connected to the sunscreen tube the identification label on the sunscreen tube is read and the data is stored and communicated to a ultraviolet monitor. The data includes the UVA and UVB sun protection factors of the sunscreen, the type of sunscreen, the brand of sunscreen, the volume of sunscreen in the sunscreen tube, and a unique identifier for the sunscreen tube. When the user applies sunscreen from the sunscreen dispenser system the dispensing cap records the time, date, and amount of sunscreen dispensed and communicates this information to the ultraviolet monitor. When the sunscreen tube runs low on sunscreen, the cap communicates a signal to the ultraviolet monitor that the sunscreen tube is low on sunscreen, allowing the ultraviolet monitor to notify the user that she is nearly out of sunscreen and to offer the user the option of re-ordering the specific sunscreen contained in the sunscreen tube or another sunscreen. Furthermore, when the user disconnects the dispenser cap from the nearly empty sunscreen dispenser and then reconnects the sunscreen cap to a different sunscreen tube (with different sun protection factors or tube with more sunscreen remaining in it) the dispenser cap reads the identification label on the new tube, records the new information and the change of container tube and communicates this to the ultraviolet monitor. The ultraviolet monitor in turn uses this new information to update user sun exposure tracking information, predicted time to sunburn, sunscreen re-application timers, exposure timers, alarms, alerts, etc.

The sunscreen dispensers may include a means to measure an amount of sunscreen dispensed and/or dispense a predetermined or user-defined amount of sunscreen, and record and communicate the amount of sunscreen dispensed along with other relevant information (the specific user to whom the sunscreen was dispensed, the date and time of the dispensing, the specific information about the sunscreen, etc.). In some embodiments the sunscreen dispenser uses a volume displacement dispensing means, such as a piston type dispensing mechanism, with a fixed or adjustable volumetric stroke (e.g., in a pump type dispenser, or a container with an oil-canning type displacement). In other embodiments the sunscreen dispenser uses an electro-mechanical means to control volume dispensing (e.g., a motor driven pump). In other embodiments the sunscreen dispenser uses a sensor to detect or estimate the amount of sunscreen dispensed (e.g., a flow sensor, a pressure sensor, or a volume displacement sensing means, etc.).

12.4 Software Program

The software program is configured: to access sunscreen information on the identification label; to estimate sunscreen use based on when and how much sunscreen is dispensed from the container, the type of sunscreen, and the time and date of each dispensing event over time; to record the sunscreen use information; and to communicate the sunscreen use information to a remote ultraviolet monitor, network, server, computing platform or other device to allow a user to track and monitor his sunscreen use.

Generally, the software program can be implemented entirely or in part at the sunscreen dispenser, at a native sunscreen tracking application on the user's (or another person's, etc.) mobile computing device, and/or at a remote server to collect, compile and transform sunscreen use data collected by the sunscreen dispenser during a period of sun exposure to notify the user of sunscreen re-application times, sun exposure alerts, alarms and reminders, and to track a user's cumulative sun exposure over time to help the user avoid sunburn and skin damage and optimize the healthy aspects of sun exposure.

The software program may be implemented to read, store, associate and/or communicate different pieces of information including: sunscreen use data; sunscreen-specific information; date and time information; location information; ultraviolet irradiance information; user-specific settings; forecast ultraviolet irradiance information; and any other types of information and data available to the software program. The software program may respond to internal algorithmic instructions to perform the aforementioned tasks, or it may rely on internal or external trigger events, such as: specific times and/or dates; elapsed time; locations; calendar events; proximity to other devices or wireless communications signals; data or power connections; sensor data; algorithmically determined events based on one or more variables; or any other trigger event that the software program may have access to.

In one implementation, a sunscreen dispenser reads information from an identification label (e.g., the UVA and UVB sun protection factors of the sunscreen, the brand and manufacturer of the sunscreen, the UPC code of the sunscreen product, the volume of the sunscreen container, the expiration date of the sunscreen, the recommended application method and amount of sunscreen, the recommended re-application time intervals, and the water resistance of the sunscreen), and records this information. The sunscreen dispenser then advertises a wireless pairing protocol for use with the Bluetooth local wireless communication protocol and is paired with a smartphone. The sunscreen dispenser wakes up when a user opens the container closure and records sunscreen application including the amount of sunscreen used, the time and the date of use, and communicates this information along with the information read from the identification label to the smartphone. The smartphone then updates the user's sunscreen use history and uses this information to reset the sunscreen re-application timer, and it checks to make sure the user applied an appropriate amount of sunscreen based on the recommended sunscreen use information and informs the user if more sunscreen is required for effective sun protection.

In a similar implementation the sunscreen dispenser communicates the sunscreen UPC code to an ultraviolet monitor. Then ultraviolet monitor uses this information to access a database with detailed sunscreen information based on the UPC code.

In another implementation the sunscreen dispenser records the number of sunscreen applications and the volume of sunscreen used from a sunscreen container, and tracks when the sunscreen container is running low on sunscreen. The sunscreen dispenser communicates a "low volume" message to the user's smartphone, and the smartphone notifies the user of the low sunscreen state of the dispenser, and offers the user the option to re-order more sunscreen from an e-commerce website, or accesses a map and database to locate a retail vendor in the user's local area that sells the same or a different sunscreen so the user can easily find and purchase more when needed.

In another implementation the sunscreen container includes an LED indicator light and an audible indicator tone to remind a user when to apply sunscreen, based on past usage history.

In yet another implementation a sunscreen dispenser includes an RFID reader, capable of reading RFID tags at close range (e.g., several inches or a few feet away). A user of the sunscreen dispenser wears ultraviolet monitor on his wrist which includes an ultraviolet irradiance sensor, a feedback mechanism (e.g., an audible tone, a graphical display screen, a vibration actuator, etc.), an RFID tag, and which is in wireless communication with the sunscreen dispenser as well as a remote computing platform, such as a smartphone. When a user dispenses sunscreen the sunscreen dispenser reads the RFID tag of the user and records the use and sunscreen information and associates it with that specific user. The dispenser communicates this information to the user's wrist worn ultraviolet monitor and/or the user's smartphone to allow the ultraviolet monitor to track sunscreen use, and provide the user with reminders to re-apply sunscreen, as well as alarms, alerts, and other information. In this manner several different users may use the sunscreen dispenser and each user can track his own sunscreen use independent of the sunscreen use of the other users, thus avoiding confusion about sunscreen application use history and re-application timers and reminders, etc. In this example, a family can share a single sunscreen dispenser and each family member can track his or her own sunscreen use to track effective sunscreen use for each individual.

The software program can implement the foregoing methods and techniques substantially in real time in order to provide the user (one or more users) with real-time feedback and guidance related to the user's sunscreen use in order to track sunscreen use and report on sunscreen use and detailed sunscreen information.

Alternatively, the software program can implement the foregoing methods and techniques asynchronously—such as when the user downloads data from the sunscreen dispenser to her smartphone upon conclusion of the current sun exposure event (some period of time spent exposed to direct and/or indirect solar irradiation) in order to inform the user when and how to adjust her future sun exposure and sunscreen use practices, which may help the user avoid sunburn, skin damage, and help reduce the risks of long term effects like skin cancer, etc.

However, the software program can process sunscreen events and usage data (e.g., closure opening, dispensing, proximity, etc.) collected by the sunscreen dispenser and provide related guidance to the user (or users) in any other way or according to any other schema and may not be considered limited to the descriptions and embodiments and implementations described herein.

12.5 Variations

Variations of the sunscreen dispenser can include one or more of the aforementioned elements (e.g., a sunscreen container; an ID label; a mounting means; a housing; a sunscreen dispensing means, one or more sensors, a communication means, a power supply, and a software program, etc.) as well as systems in which one or more of the aforementioned elements are mounted on, assembled to, connected to or otherwise used in combination with other devices or objects.

Figure 4:
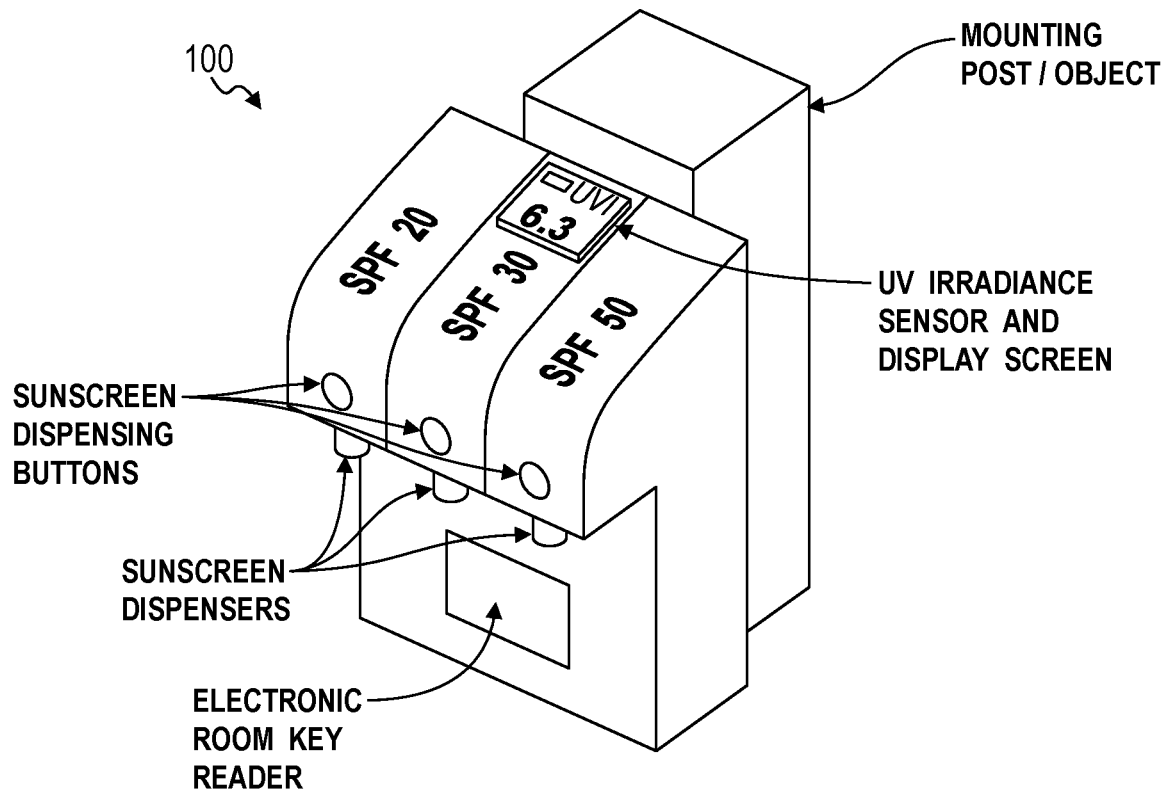
FIG. 4 is a graphical representation of one variation of the dispenser system.

In one variation shown in FIG. 4, the dispenser system 100 is implemented with a sunscreen dispenser mounted on and affixed to a post (or other object) at a beach hotel and resort, and includes: an electronic room key reader; three individual sunscreen containers with three different sunscreens (of varying sun protection factor values, water resistance, etc.); a means to dispense said sunscreens; and a ultraviolet irradiance sensing means. Upon registration at the hotel and resort a hotel guest registers the phone number of her personal smartphone, which is stored in association with her registration information and her electronically readable room key in a central database at the hotel and resort. When the guest decides to go outside to the beach, she stops at the sunscreen dispenser, which (by means of the ultraviolet irradiance sensor means) informs the guest of the current ultraviolet irradiance and recommends a specific sunscreen to use for the current and forecast conditions. The guest uses her room key to access the sunscreen dispenser, selects the sunscreen she prefers to use, the sunscreen dispenser dispenses an amount of sunscreen to the user and then records the date, time, the user's room key identification, the amount of sunscreen dispensed, and the type of sunscreen (e.g., the SPF, etc.), and sends this information to the hotel's central database. The hotel's computer server then tracks the guest's sunscreen use and sends text messages to her smartphone when it is time re-apply more sunscreen, when the user may seek shade, when the ultraviolet irradiance is too high to remain outdoors, as well as other reminders, alarms, alerts, etc. (e.g., reminders for spa treatments, incoming hotel messages, safety warnings, etc.). In this manner a hotel or resort may install one or more networked sunscreen dispensers in locations suitable to meet its guest's needs for sunscreen use during their stay, such as near the swimming pool, near the beach, at an outdoor café, or any other location.

Figure 5:
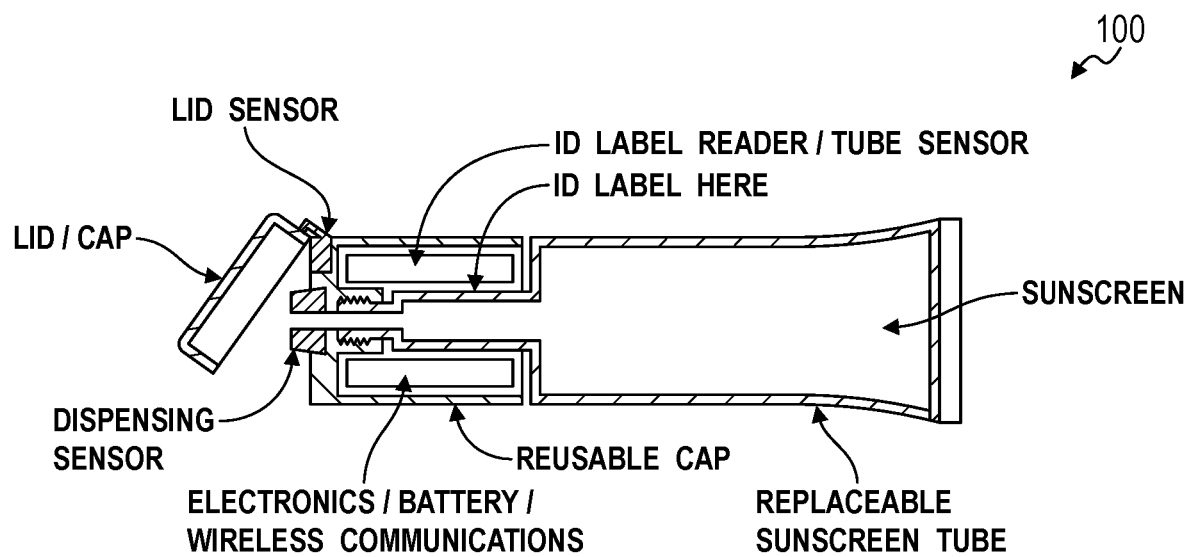
FIG. 5 is a graphical representation of one variation of the dispenser system.

In another implementation shown in FIG. 5 (section view), the dispenser system 100 includes a sunscreen dispenser configured to connect to a replaceable tube of sunscreen, where the sunscreen container includes: a re-usable cap configured with a sunscreen dispensing means and configured to connect to a replaceable sunscreen tube; a means to sense sunscreen dispensing; a means to detect the state of a lid or cap closure; a means to detect and/or identify a replaceable sunscreen tube; a wireless communication means configured to output information about said container and events detected by said sensor; a power supply to power the electronic elements of the system (e.g., a battery or a solar cell); and a software program. The sunscreen dispenser is configured to connect to the sunscreen tube in such a manner as to allow; the sunscreen tube to detect and/or identify the sunscreen tube and the sun protection factors, type of sunscreen within the tube, and other sunscreen specific information; to allow the sunscreen tube to dispense sunscreen; and to enable the sunscreen dispenser to detect when sunscreen is dispensed, record the dispensing event(s), and communicate the sunscreen use (along with sunscreen information, date and time) to a remote portable computing platform, smartphone, watch, activity tracker, ultraviolet monitor or other device. The sunscreen dispenser may be connected to a sunscreen tube and can monitor sunscreen use. When the tube is empty, the empty tube may be disconnected from the sunscreen dispenser and a new tube may be connected. The sunscreen dispenser can record the changed sunscreen tube, and continue to monitor sunscreen use with the new tube attached. In this manner the sunscreen dispenser system may be reusable for more than one sunscreen tube, and accurately track sunscreen use from one tube to the next, recording and communicating changes in sunscreen SPF, sunscreen type, etc.

In another implementation, the sunscreen dispenser includes a photovoltaic solar cell that is configured to power the sunscreen dispenser and/or charge an internal battery (or capacitor etc.). In this manner the sunscreen dispenser does not require the replacement of batteries since the system self-powers/recharges when exposed to bright light, such as sunlight, etc.

Figure 6:
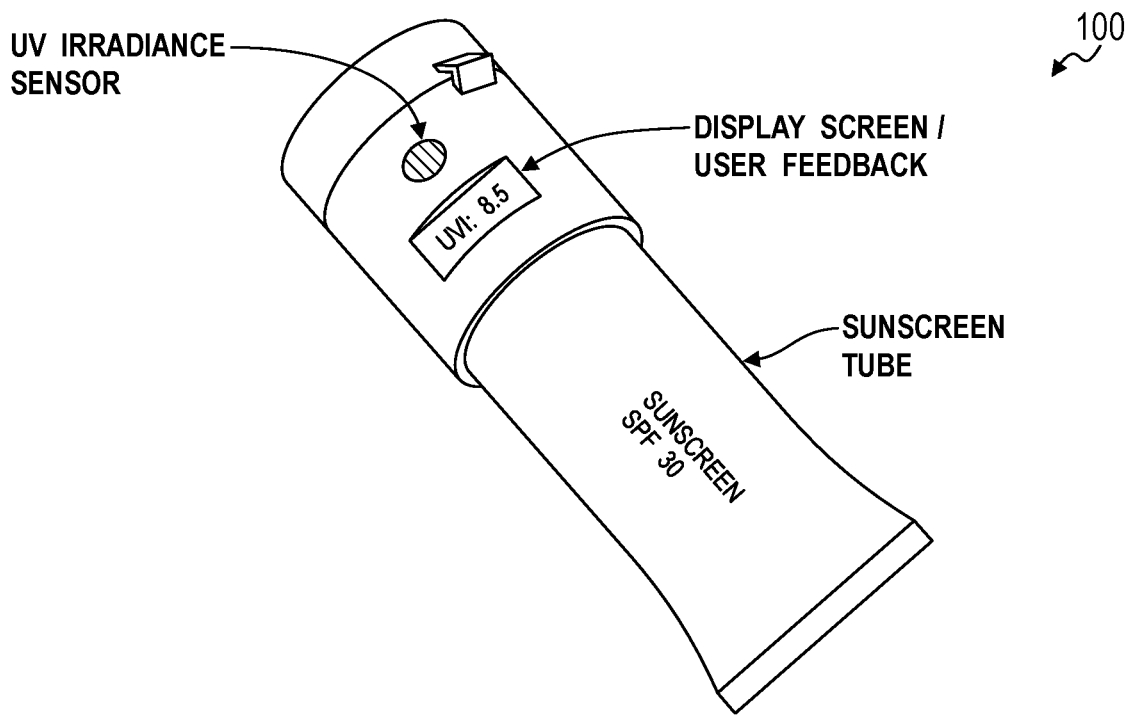
FIG. 6 is a graphical representation of one variation of the dispenser system.

In another implementation, shown in FIG. 6, the sunscreen dispenser is configured to include: a ultraviolet monitor affixed to or incorporated into the sunscreen dispenser in such a manner that the sunscreen dispenser may be used to detect the ultraviolet irradiance; and a user interface that includes, but is not limited to, a display screen. In this manner the ultraviolet monitor may read the ultraviolet irradiance directly and offer the user guidance, feedback, reminders, timers, etc. related to sunscreen use, sun protection and ultraviolet irradiation or ultraviolet irradiance levels specific to the location of the sunscreen dispenser. By combining the ultraviolet monitor and the sunscreen dispenser the user is able to access real time ultraviolet conditions (like ultraviolet irradiance), benefit from reminders and guidance for sunscreen application and sun protection, and have access to sunscreen on one integrated sunscreen dispenser configuration.

Figure 7:
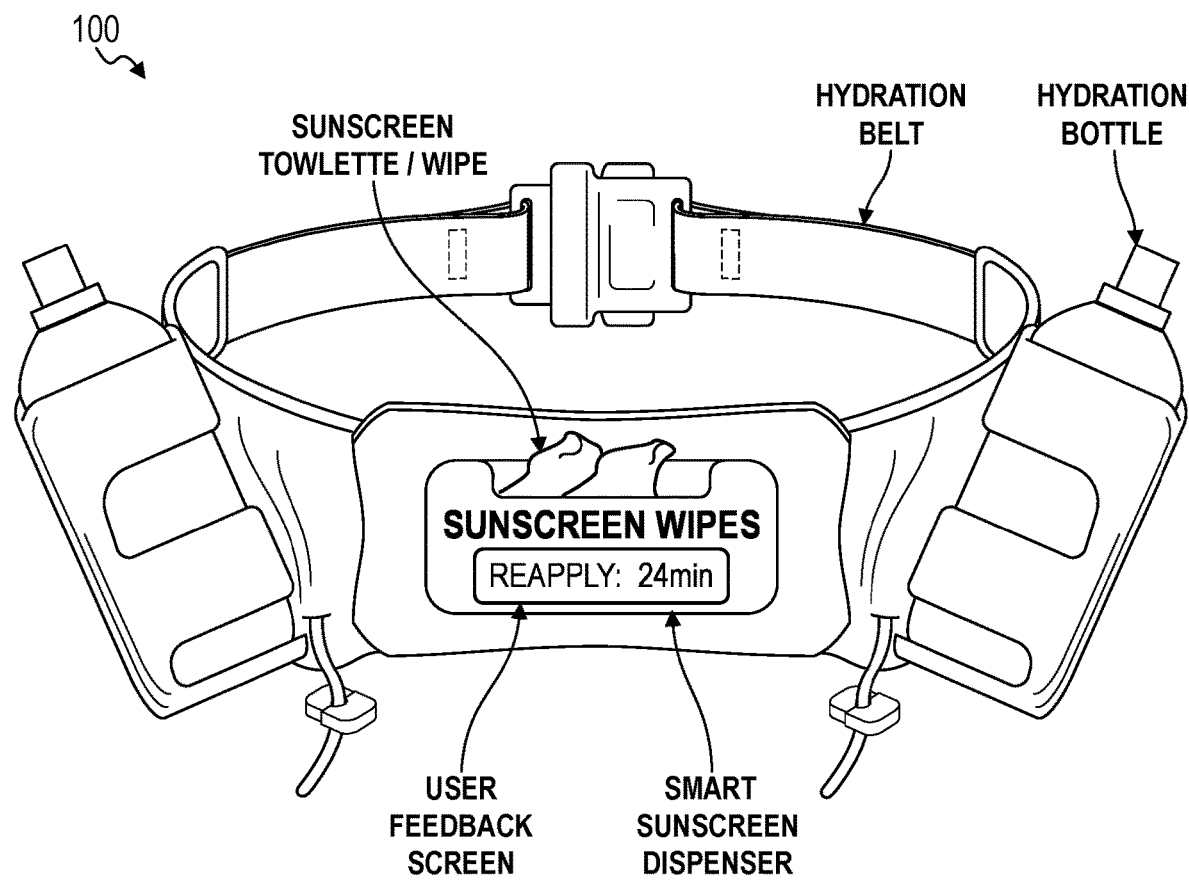
FIG. 7 is a graphical representation of one variation of the dispenser system.

In another implementation shown in FIG. 7, the dispenser system 100 includes a sunscreen dispenser system configured to include: a sunscreen dispenser that may be affixed to a runner's hydration and fuel belt; and a wrist-worn ultraviolet monitor that is in communication with said sunscreen dispenser. The sunscreen dispenser is configured to include:

a connection means to attach to a hydration and fuel belt; a sunscreen container with multiple single-use sunscreen towlettes (or wipes); a dispensing means for dispensing said towlettes (or wipes); a means for detecting a dispensing event of a towlette (or wipe); a wireless communication means configured to output information about said container, sunscreen, and events detected by said means for detecting a dispensing event; a power supply to power the electronic elements of the system (e.g., a battery and/or a solar cell); and a software program. The sunscreen dispenser may be worn by an athlete (e.g., a runner, a hiker, a cyclist, a kayaker, a golfer, a skier, a snowboarder, or any other individual engaged in an outdoor activity) in an easily accessible location (e.g., on a hydration and fuel belt, backpack, bicycle, kayak, etc.) and the sunscreen dispenser is configured to detect when a sunscreen towlette (or wipe) is used, record the use information along with the associated time and date of the event, and to communicate this information (along with sunscreen specific information) to a ultraviolet monitor, smartphone, watch, bike computer, portable computing platform, running watch, server, etc. In this manner an athlete, for example, may access her sunscreen without the need to stop running, and without the need to manually record the sunscreen application event, while the sunscreen system automatically updates the user's sunscreen use information and the wrist-worn ultraviolet monitor (after receiving information from the sunscreen dispenser) tracks the users sun exposure and sunscreen use, offers the user reminders to reapply sunscreen, advice and guidance about safe and effective sun exposure and sunscreen use, warnings, alerts, alarms etc. By using the sunscreen dispenser system the user is provided with accurate sunscreen use tracking during her athletic activities (i.e. running). The sunscreen dispenser system may be used during any activity, including cycling, golf, walking hiking, kayaking, sailing, tennis, skiing, snowboarding, etc. where the user may experience sun exposure and would benefit from the features of the system.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the FIGUREs and claims, modifications and changes can be made to the embodiments of the invention without departing from the scope of this invention as defined in the following claims.

I claim:

1. A method comprising:
accessing a skin type of a user;
predicting a first set of locations occupied by the user during a first future time interval;
based on historical ultraviolet radiation irradiance data and the first future time interval, calculating a first predicted unprotected ultraviolet radiation exposure of the user during the first future time interval;
selecting a first sunscreen formula based on the first predicted unprotected ultraviolet radiation exposure and the skin type of the user; and
supplying a first volume of the first sunscreen formula to the user.

2. The method of claim 1, wherein accessing the skin type of the user comprises:
accessing a digital photographic image, of the face of the user, recorded by a mobile computing device associated with the user;
detecting a region of the photographic image depicting a face;
extracting an eye color from the region of the photographic image;
extracting a hair color from the region of the photographic image;
extracting a constitutional skin color from the region of the photographic image;
extracting a proportion of pigment cell clusters from the region of the photographic image; and
based on the eye color, the hair color, the constitutional skin color, and the proportion of pigment cell clusters extracted from the region of the photographic image, calculating the skin type of the user.

3. The method of claim 1:
wherein predicting the first set of locations occupied by the user during the first future time interval comprises, during initial setup of a user profile for the user, accessing a geospatial location of a mobile computing device associated with the user;
further comprising, during initial setup of the user profile for the user, serving a survey, to the mobile computing device, for a first set of outdoor activities and durations of time commonly spent by the user performing activities in the first set of outdoor activities during a current time of year; and
wherein calculating the first predicted unprotected ultraviolet radiation exposure of the user during the first future time interval comprises:
accessing the historical ultraviolet radiation irradiance data for a geographic region containing the geospatial location; and
calculating the first predicted unprotected ultraviolet radiation exposure based on the historical ultraviolet radiation irradiance data for the geographic region and durations of time planned for performing activities in the first set of outdoor activities contained in results of the survey.

4. The method of claim 3:
wherein accessing the historical ultraviolet radiation irradiance data for the geographic region comprises accessing a first time series of ultraviolet radiation irradiances within the geographic region over a one-month period preceding the first future time interval by one year; and
wherein calculating the first predicted unprotected ultraviolet radiation exposure comprises:
predicting exposed skin area of the user during periods of activities in the first set of outdoor activities based on activity type; and integrating the first time series of ultraviolet radiation irradiances over the first future time interval spanning one month based on times of day, durations, and predicted exposed skin area of activities in the first set of outdoor activities to calculate the first predicted unprotected ultraviolet radiation exposure.

5. The method of claim 3, wherein selecting the first sunscreen formula comprises:
  in response to the first set of outdoor activities comprising swimming in a pool, selecting the first sunscreen formula comprising a pool-safe sunscreen formula;
  in response to the first set of outdoor activities comprising an outdoor sport, selecting the first sunscreen formula comprising a sweat-resistant sunscreen formula; and
  in response to the first set of outdoor activities comprising occupying a beach, selecting the first sunscreen formula comprising an eco-friendly sunscreen formula.

6. The method of claim 1, wherein selecting the first sunscreen formula comprises:
  calculating a maximum allowable ultraviolet radiation exposure for periods within the first future time interval based on the skin type of the user;
  calculating a first minimum sun protection factor predicted to reduce the first predicted unprotected ultraviolet radiation exposure to less than the maximum allowable ultraviolet radiation exposure for periods within the first future time interval; and
  selecting the first sunscreen formula characterized by a first sun protection factor greater than the first minimum sun protection factor.

7. The method of claim 6:
  further comprising:
    querying the user for confirmation of a skin sensitivity; and
    querying the user for a first set of outdoor activities commonly performed by the user during a current time of year; and
  wherein selecting the first sunscreen formula comprises:
    isolating a first subset of sunscreen formulas, in a population of existing sunscreen formulas, excluding components known to irritate the skin sensitivity;
    isolating a second subset of sunscreen formulas, in the first subset of sunscreen formulas, characterized by sun protection factors greater than the first minimum sun protection factor;
    isolating a third subset of sunscreen formulas, in the second subset of sunscreen formulas, tailored for activities in the first set of outdoor activities; and
    selecting the first sunscreen formula from the third subset of sunscreen formulas.

8. The method of claim 6:
  further comprising:
    querying the user for confirmation of a skin sensitivity; and
    querying the user for a first set of outdoor activities commonly performed by the user during a particular time of year;
  wherein selecting the first sunscreen formula comprises inserting the first minimum sun protection factor, the skin sensitivity, and the first set of outdoor activities into a sunscreen formula model to calculate a first set of proportions of a set of sunscreen components; and
  wherein supplying the first volume of the first sunscreen formula to the user comprises:
    manufacturing the first volume of the first sunscreen formula according to the first set of proportions of the set of sunscreen components; and
    shipping the first volume to the user prior to the first future time interval.

9. The method of claim 6:
  further comprising, during initial setup of a user profile for the user, serving a prompt, to the user via a mobile computing device, to select a sun-related goal from a set of sun-related goals comprising: reducing long-term skin cancer risk; preventing sun burn; maintaining vitamin-D levels; and increasing tan; and
  wherein calculating the maximum allowable ultraviolet radiation exposure for the duration of the first future time interval further comprises:
    decreasing the maximum allowable ultraviolet radiation exposure responsive to selection of reducing long-term skin cancer risk by the user;
    decreasing the maximum allowable ultraviolet radiation exposure as a function of the skin type of the user responsive to selection of preventing sun burn by the user;
    increasing the maximum allowable ultraviolet radiation exposure as a function of age of the user responsive to selection of maintaining vitamin-D levels by the user; and
    increasing the maximum allowable ultraviolet radiation exposure responsive to selection of increasing tan by the user.

10. The method of claim 6, further comprising:
  during the first future time interval, recording a time series of actual ultraviolet irradiances detected by a mobile computing device comprising an ultraviolet sensor configured to detect intensity of incident ultraviolet radiation;
  integrating the time series of actual ultraviolet irradiances over a duration of the first future time interval to calculate a first actual unprotected ultraviolet radiation exposure of the user during the first future time interval;
  predicting a second set of locations occupied by the user during a second future time interval succeeding the first future time interval;
  based on historical ultraviolet radiation data and the second set of locations, calculating a second predicted unprotected ultraviolet radiation exposure of the user during the second future time interval;
  in response to the first actual unprotected ultraviolet radiation exposure exceeding the first predicted unprotected ultraviolet radiation exposure, increasing the second predicted unprotected ultraviolet radiation exposure;
  calculating a second minimum sun protection factor predicted to reduce the second predicted unprotected ultraviolet radiation exposure to less than the maximum allowable ultraviolet radiation exposure;
  selecting a second sunscreen formula, different from the first sunscreen formula, characterized by a second sun protection factor greater than the second minimum sun protection factor; and
  supplying a second volume of the second sunscreen formula to the user.

11. The method of claim 10:
  further comprising, during the first future time interval:
    accessing a first location of the mobile computing device;
    tracking an orientation of the mobile computing device;
    during a first sampling interval:
      in response to the orientation of the mobile computing device approximately aligning with a target direct orientation facing the Sun at a first time, recording a first ultraviolet value read from the ultraviolet sensor at approximately the first time as a direct ultraviolet value;

in response to the orientation of the mobile computing device approximately falling within a target diffuse orientation window biased away from the Sun at a second time, recording a second ultraviolet value read from the ultraviolet sensor at approximately the second time as a diffuse ultraviolet value;

in response to the orientation of the mobile computing device approximately aligning with a target global orientation facing vertically upward at a third time, recording a third ultraviolet value read from the ultraviolet sensor at approximately the third time as a global ultraviolet value; and calculating a first ultraviolet irradiance proximal the mobile computing device at the first location during the first sampling interval based on a combination of the direct ultraviolet value, the diffuse ultraviolet value, and the global ultraviolet value;

during a second sampling interval:

in response to the orientation of the mobile computing device approximately aligning with a target direct orientation facing the Sun at a second time, recording a second ultraviolet value read from the ultraviolet sensor at approximately the second time as a direct ultraviolet value;

in response to the orientation of the mobile computing device approximately falling within a target diffuse orientation window biased away from the Sun at a second time, recording a second ultraviolet value read from the ultraviolet sensor at approximately the second time as a diffuse ultraviolet value;

in response to the orientation of the mobile computing device approximately aligning with a target global orientation facing vertically upward at a third time, recording a third ultraviolet value read from the ultraviolet sensor at approximately the third time as a global ultraviolet value; and calculating a second ultraviolet irradiance proximal the mobile computing device at the second location during the second sampling interval based on a combination of the direct ultraviolet value, the diffuse ultraviolet value, and the global ultraviolet value; and wherein integrating the time series of actual ultraviolet indices over the duration of the first future time interval comprises:

calculating an integral between the first ultraviolet irradiance and the second ultraviolet irradiance from the first sampling interval to the second sampling interval; and incorporating the integral into the first actual unprotected ultraviolet radiation exposure of the user during the first future time interval.

12. The method of claim 6, further comprising:
during the first future time interval:
recording confirmation of application of sunscreen, from the first volume of the first sunscreen formula, by the user via a mobile computing device;
recording presence of sunburn from the user via the mobile computing device;
predicting a second set of locations occupied by the user during a second future time interval succeeding the first future time interval;
based on historical ultraviolet radiation irradiance data and the second set of locations, calculating a second predicted unprotected ultraviolet radiation exposure of the user during the second future time interval;
calculating a second minimum sun protection factor predicted to reduce the second predicted unprotected ultraviolet radiation exposure to less than the maximum allowable ultraviolet radiation exposure;
in response to confirmation of application of sunscreen and presence of sunburn from the user during the first future time interval, increasing the second minimum sun protection factor;
selecting a second sunscreen formula, different from the first sunscreen formula, characterized by a second sun protection factor greater than the second minimum sun protection factor; and
supplying a second volume of the second sunscreen formula to the user.

13. The method of claim 6, further comprising:
during the first future time interval, receiving confirmation from the user of a plan to visit a new location during a first subinterval of the first future time interval, the new location excluded from the first set of locations;
based on historical ultraviolet radiation irradiance data for the new location and a duration of the first subinterval, calculating a second predicted unprotected ultraviolet radiation exposure of the user during the first subinterval;
calculating a second minimum sun protection factor predicted to reduce the second predicted unprotected ultraviolet radiation exposure to less than the maximum allowable ultraviolet radiation exposure; and
in response to the second minimum sun protection factor exceeding the first sun protection factor of the first sunscreen formula:
selecting a second sunscreen formula characterized by a second sun protection factor greater than the second minimum sun protection factor; and
shipping a second volume of the second sunscreen formula to the user prior to the first subinterval during the first future time interval.

14. The method of claim 1:
wherein predicting the first set of locations occupied by the user during the first future time interval comprises:
accessing a digital calendar associated with the user;
extracting the first set of locations and a corresponding first set of outdoor activities from a set of events contained in the digital calendar;
wherein calculating the first predicted unprotected ultraviolet radiation exposure of the user during the first future time interval comprises, for each location in the first set of locations, calculating a predicted unprotected ultraviolet radiation exposure at the location based on historical ultraviolet radiation irradiance data for the location, a duration of a corresponding activity in the corresponding first set of outdoor activities, and an exposed skin area typical of the corresponding activity; and
wherein selecting the first sunscreen formula comprises selecting the first sunscreen formula based on predicted unprotected ultraviolet radiation exposures at each location in the first set of locations.

15. The method of claim 1:
wherein calculating the first predicted unprotected ultraviolet radiation exposure of the user during the first future time interval comprises, for each day within the first future time interval spanning a period of one month, calculating a predicted unprotected ultraviolet radiation exposure of the user based on predicted durations of time spent by the user at a subset of locations, in the first set of locations, during the day;
wherein selecting the first sunscreen formula comprises:
calculating a maximum allowable ultraviolet radiation exposure per day for the user based on the skin type of the user;
estimating a maximum predicted unprotected ultraviolet radiation exposure per day within the first future time interval;
calculating a first minimum sun protection factor predicted to reduce the maximum predicted unprotected ultraviolet radiation exposure per day within the first future time interval to less than the maximum allowable ultraviolet radiation exposure; and
selecting the first sunscreen formula characterized by a first sun protection factor greater than the first minimum sun protection factor; and
wherein supplying the first volume of the first sunscreen formula to the user comprises shipping the first volume approximating a one-month supply of the first sunscreen formula to an address associated with the user.

16. The method of claim 1:
further comprising, during initial setup of a user profile for the user on a sunscreen supply platform:
accessing a geospatial location of a mobile computing device associated with the user;
collecting, via the mobile computing device, demographic information of the user; and
surveying the user, via the mobile computing device, for a first set of outdoor activities planned for a current time of year; and
wherein predicting the first set of locations occupied by the user during the first future time interval and calculating the first predicted unprotected ultraviolet radiation exposure of the user during the first future time interval comprises:
identifying a cohort of users, on the sunscreen supply platform, associated with demographic information similar to demographic information of the user, associated with a geographic region containing the geospatial location of the mobile computing device, and associated with outdoor activities similar to a first set of outdoor activities;
predicting the first set of locations based on types and durations of locations frequented by the cohort of users;
calculating the first predicted unprotected ultraviolet radiation exposure of the user during the first future time interval based on actual ultraviolet indices detected by ultraviolet sensors, associated with the cohort of users, when occupying locations similar to the first set of locations.

17. The method of claim 1, further comprising:
predicting a second set of locations occupied by the user during a second future time interval succeeding the first future time interval;
based on historical ultraviolet radiation data and the second future time interval, calculating a second predicted unprotected ultraviolet radiation exposure of the user during the second future time interval; and
in response to the second predicted unprotected ultraviolet radiation exposure falling below a threshold ultraviolet radiation exposure, supplying a vitamin-D supplement to the user for the second future time interval in place of a sunscreen formula.

18. The method of claim 1, further comprising, on a current day within the first future time interval:
at a mobile computing device associated with the user and comprising an ultraviolet sensor configured to detect intensity of incident ultraviolet radiation:
accessing a current location of the mobile computing device;
based on the current location of the mobile computing device, a current time, and a current date, calculating a target direct orientation of the mobile computing device for which a primary axis of the ultraviolet sensor is approximately normal to the sun;
tracking an orientation of the mobile computing device;
in response to the orientation of the mobile computing device approximately aligning with the target direct orientation at the current time, storing a current value read from the ultraviolet sensor at approximately the current time as a current direct ultraviolet value;
calculating a current ultraviolet irradiance proximal a current location of the mobile computing device at the current time based on the current direct ultraviolet value;
tracking a cumulative unprotected ultraviolet radiation exposure of the user on the current day based on the current ultraviolet irradiance and preceding ultraviolet irradiance values calculated at the mobile computing device on the current day;
in response to the cumulative unprotected ultraviolet radiation exposure exceeding a threshold unprotected ultraviolet radiation exposure, serving a prompt to the user to apply the first sunscreen formula.

19. The method of claim 18, further comprising, on the current day:
calculating a maximum allowable ultraviolet radiation exposure per day for the user based on the skin type of the user;
receiving confirmation from the user, via the mobile computing device, of application of the first sunscreen formula at a first time;
tracking actual cumulative ultraviolet radiation exposure of the user on the current day based on the cumulative unprotected ultraviolet radiation exposure on the current day up to the first time and the cumulative unprotected ultraviolet radiation exposure on the current day after the first time adjusted based on an initial sun protection factor of the first sunscreen formula and a half-life of the first sunscreen formula; and
in response to the actual cumulative ultraviolet radiation exposure of the user on the current day exceeding the maximum allowable ultraviolet radiation exposure per day for the user, serving a prompt to the user to seek shelter from the Sun.

20. A method comprising:
accessing a skin type of a user;
predicting a first set of locations occupied by the user during a first future time interval;
based on historical ultraviolet irradiance data and the first future time interval, calculating a first predicted unprotected ultraviolet radiation exposure of the user during the first future time interval;

calculating a maximum allowable ultraviolet radiation exposure for periods within the first future time interval based on the skin type of the user;

calculating a first minimum sun protection factor predicted to reduce the first predicted unprotected ultraviolet radiation exposure to less than the maximum allowable ultraviolet radiation exposure;

selecting a first sunscreen formula characterized by a first sun protection factor greater than the first minimum sun protection factor; and shipping the first volume of the first sunscreen formula to the user prior to the first future time interval.

* * * * *